United States Patent
Lechner et al.

(10) Patent No.: US 12,377,034 B2
(45) Date of Patent: *Aug. 5, 2025

(54) METHOD FOR DYEING KERATINOUS MATERIAL, COMPRISING THE USE OF AN ORGANOSILICON COMPOUND, AN EFFECT PIGMENT AND A FILM-FORMING POLYMER II

(71) Applicant: Henkel AG & Co. KGaA, Duesseldorf (DE)

(72) Inventors: Torsten Lechner, Langenfeld (DE); Gabriele Weser, Neuss (DE); Claudia Kolonko, Remscheid (DE); Caroline Kriener, Duesseldorf (DE); Ulrike Schumacher, Duesseldorf (DE); Marc Nowottny, Monchengladbach (DE); Juergen Schoepgens, Schwalmtal (DE); Phillip Jaiser, Langenfeld (DE); Carsten Mathiaszyk, Essen (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 793 days.

This patent is subject to a terminal disclaimer.

(21) Appl. No.: 17/440,703

(22) PCT Filed: Mar. 13, 2020

(86) PCT No.: PCT/EP2020/056793
§ 371 (c)(1),
(2) Date: Sep. 17, 2021

(87) PCT Pub. No.: WO2020/187727
PCT Pub. Date: Sep. 24, 2020

(65) Prior Publication Data
US 2022/0168205 A1  Jun. 2, 2022

(30) Foreign Application Priority Data

Mar. 19, 2019 (DE) .......................... 102019203677.5

(51) Int. Cl.
*A61K 8/58* (2006.01)
*A61K 8/26* (2006.01)
*A61K 8/81* (2006.01)
*A61Q 5/06* (2006.01)

(52) U.S. Cl.
CPC ............... *A61K 8/585* (2013.01); *A61K 8/26* (2013.01); *A61K 8/8152* (2013.01); *A61K 8/8158* (2013.01); *A61K 8/8176* (2013.01); *A61Q 5/065* (2013.01); *A61K 2800/436* (2013.01); *A61K 2800/884* (2013.01)

(58) Field of Classification Search
CPC ........ A61K 8/585; A61K 8/26; A61K 8/8152; A61K 8/8158; A61K 8/8176; A61K 2800/436; A61K 2800/884; A61Q 5/065
See application file for complete search history.

(56) References Cited

U.S. PATENT DOCUMENTS

| | | | | |
|---|---|---|---|---|
| 11,504,321 B2* | 11/2022 | Lechner | .................... | A61K 8/26 |
| 11,654,095 B2* | 5/2023 | Krohn | ...................... | A61K 8/19 |
| | | | | 8/425 |
| 11,701,318 B2* | 7/2023 | Lechner | .................... | A61K 8/26 |
| | | | | 8/425 |
| 11,744,789 B2* | 9/2023 | Lechner | .................... | A61K 8/25 |
| | | | | 8/425 |
| 11,766,390 B2* | 9/2023 | Lechner | ................. | A61Q 5/065 |
| | | | | 8/405 |
| 11,826,586 B2* | 11/2023 | Jaiser | ....................... | A61K 8/44 |
| 11,890,366 B2* | 2/2024 | Jaiser | ..................... | A61Q 5/065 |
| 11,896,701 B2* | 2/2024 | Jaiser | .................... | A61K 8/602 |
| 11,918,665 B2* | 3/2024 | Lechner | ................ | A61K 8/894 |
| 11,938,211 B2* | 3/2024 | Lechner | ............... | A61K 8/8147 |
| 11,992,546 B2* | 5/2024 | Lechner | ................... | A61Q 5/06 |
| 12,048,756 B2* | 7/2024 | Krohn | ...................... | A61K 8/34 |
| 12,090,222 B2* | 9/2024 | Weser | ...................... | A61Q 5/08 |
| 2010/0083446 A1* | 4/2010 | Brun | ..................... | A61K 8/891 |
| | | | | 8/405 |

(Continued)

FOREIGN PATENT DOCUMENTS

| | | |
|---|---|---|
| CN | 104244913 A | 12/2014 |
| CN | 107567484 A | 1/2018 |

(Continued)

OTHER PUBLICATIONS

Technical Data Sheet, Alegrace Gorgeous 03-02, Oct. 12, 2018 (Oct. 12, 2018), Retrieved from the Internet: https://asia.in-cosmetics.com/_novadocuments/526923?v=636760724862900000 [retrieved on May 25, 2020], XP055697995.

*Primary Examiner* — Blessing M Fubara
(74) *Attorney, Agent, or Firm* — Ingrassia Fisher & Lorenz, LLP

(57) ABSTRACT

The subject of the present disclosure is a process for dyeing keratinous material, in particular human hair, comprising the following steps:

application of an agent (a) to the keratinous material, the agent (a) comprising at least one organic silicon compound, and Application of an agent (b) to the keratinous material, wherein the agent (b) comprises:

(b1) at least one colorant compound comprising at least one lenticular substrate platelet-based pigment, and (b2) at least one film-forming polymer.

The application also discloses a multi-component packaging unit which contains the two agents (a) and (b) in two separately packaged containers.

7 Claims, No Drawings

(56) References Cited

U.S. PATENT DOCUMENTS

| | | |
|---|---|---|
| 2015/0080338 A1 | 3/2015 | Lorant et al. |
| 2015/0098972 A1* | 4/2015 | Schumacher ............ A61Q 1/06 427/299 |
| 2015/0258004 A1* | 9/2015 | Plos ..................... A61K 8/8111 132/203 |
| 2016/0168387 A1 | 6/2016 | Shimizu et al. |
| 2016/0235657 A1 | 8/2016 | Herrlein et al. |
| 2017/0355855 A1 | 12/2017 | Gruener et al. |
| 2018/0112076 A1 | 4/2018 | Huber et al. |

FOREIGN PATENT DOCUMENTS

| | | | |
|---|---|---|---|
| DE | 102004006145 A1 | 8/2005 | |
| EP | 2168633 A2 * | 3/2010 | ............... A61K 8/31 |
| EP | 3081601 A1 | 10/2016 | |
| GB | 2562021 A | 11/2018 | |
| JP | 2010083892 A | 4/2010 | |
| JP | 2016536406 A | 11/2016 | |
| JP | 2020505441 A | 2/2020 | |
| JP | 2021523141 A | 9/2021 | |
| WO | 2018130912 A1 | 7/2018 | |
| WO | 2018185345 A1 | 10/2018 | |

\* cited by examiner

METHOD FOR DYEING KERATINOUS MATERIAL, COMPRISING THE USE OF AN ORGANOSILICON COMPOUND, AN EFFECT PIGMENT AND A FILM-FORMING POLYMER II

CROSS-REFERENCE TO RELATED APPLICATION

This application is a U.S. National-Stage entry under 35 U.S.C. § 371 based on International Application No. PCT/EP2020/056793, filed Mar. 13, 2020, which was published under PCT Article 21(2) and which claims priority to German Application No. 102019203677.5, filed Mar. 19, 2019, which are all hereby incorporated in their entirety by reference.

TECHNICAL FIELD

The subject of the present application is a process for dyeing keratinous material, in particular human hair, which comprises the application of two different agents (a), and (b). The agent (a) contains at least one organic silicon compound. The agent (b) contains at least one color-imparting compound comprising at least one selected pigment.

The second subject-matter of this application is a multi-component packaging unit (kit-of-parts) for coloring keratinous material, in particular human hair, which comprises the agents (a) and (b) separately packaged in two different containers.

BACKGROUND

Changing the shape and color of keratinous material, especially human hair, is an important area of modern cosmetics. To change the hair color, the expert knows various coloring systems depending on the coloring requirements. Oxidation dyes are usually used for permanent, intensive dyeing's with good fastness properties and good grey coverage. Such colorants contain oxidation dye precursors, so-called developer components and coupler components, which, under the influence of oxidizing agents such as hydrogen peroxide, form the actual dyes among themselves. Oxidation dyes are exemplified by very long-lasting dyeing results.

When direct dyes are used, ready-made dyes diffuse from the colorant into the hair fiber. Compared to oxidative hair dyeing, the dyeing's obtained with direct dyes have a shorter shelf life and quicker wash ability. Dyeing with direct dyes usually remain on the hair for a period of between about 5 and about 20 washes.

The use of color pigments is known for short-term color changes on the hair and/or skin. Color pigments are generally understood to be insoluble, coloring substances. These are present undissolved in the dye formulation in the form of small particles and are only deposited from the outside on the hair fibers and/or the skin surface. Therefore, they can usually be removed again without residue by a few washes with detergents comprising surfactants. Various products of this type are available on the market under the name hair mascara.

If the user desires a particularly long-lasting coloring of his hair, the use of oxidative dyes is his only option so far. However, despite numerous optimization attempts, an unpleasant ammonia or amine odor cannot be completely avoided in oxidative hair dyeing. The hair damage still associated with the use of oxidative dyes also has a negative effect on the user's hair. A continuing challenge is therefore the search for alternative, high-performance dyeing processes.

EP 2168633 B1 deals with the task of producing long-lasting hair colorations using pigments. The paper teaches that when a combination of pigment, organic silicon compound, hydrophobic polymer and a solvent is used on hair, it is possible to create colorations that are said to be particularly resistant to shampooing.

Metallic luster pigments or metallic effect pigments are widely used in many fields of technology. They are used, for example, to color coatings, printing inks, inks, plastics, glasses, ceramic products, and preparations for decorative cosmetics such as nail polish. They are exemplified above all by their attractive angle-dependent color impression (goniochromism) and their metallic-looking luster.

Hair with a metallic finish or metallic highlights are in trend. The metallic tone makes the hair look thicker and shinier.

There is a need to provide hair dyes with effect pigments that on the one hand have high wash and rub fastness and on the other hand do not negatively affect hair properties such as manageability and feel. For this purpose, it would be desirable if the effect pigments used had a high covering power and could be applied to the hair in thin layers.

BRIEF SUMMARY

Methods for dyeing keratinous material are provided, as well as a kit-of-parts for the same. In an exemplary embodiment, a method for dyeing keratinous material includes applying an agent (a) to the keratinous material, where the agent (a) includes an organic silicon compound. An agent (b) is applied to the keratinous material, where the agent (b) includes a colorant compound comprising a lenticular substrate platelet-based pigment, and a film-forming polymer.

A kit-of-parts is provided in another embodiment. The kit of parts includes a first container and a second container, where an agent (a) is contained in the first container and an agent (b) is contained in the second container. The agent (a) includes an organic silicon compound, and the agent (b) includes a colorant compound comprising a lenticular substrate platelet-based pigment and a film-forming polymer.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Accordingly, the task of the present disclosure was to provide a dyeing system that has fastness properties comparable to oxidative dyeing. In particular, the washing and rubbing fastness properties should be outstanding, but the use of the oxidation dye precursors normally used for this purpose should be avoided.

Surprisingly, it has now been found that the task can be excellently solved if keratinous materials, in particular human hair, are colored by a process in which at least two agents (a) and (b) are applied to the keratinous materials (hair). Here, the agent (a) comprises at least one organic silicon compound, and the agent (b) comprises at least one selected pigment (b1) and a film-forming polymer (b2).

When the two agents (a) and (b) were used in a dyeing process, keratinous material could be dyed with particularly high fastnesses.

A first object of the present disclosure is a method for coloring keratinous material, in particular human hair, comprising the following steps:
  application of an agent (a) to the keratinous material, the agent (a) comprising at least one organic silicon compound, and
  Application of an agent (b) to the keratinous material, wherein the agent (b) comprises: (b1) at least one color-imparting compound comprising at least one pigment based on a lenticular substrate platelet, and (b2) and at least one film-forming polymer.

Keratinous Material

Keratinous material includes hair, skin, nails (such as fingernails and/or toenails). Wool, furs, and feathers also fall under the definition of keratinous material.

Preferably, keratinous material is understood to be human hair, human skin, and human nails, especially fingernails and toenails. Keratinous material is understood to be human hair.

Agent (a) and (b)

In the procedure as contemplated herein, agents (a) and (b) are applied to the keratinous material, in particular human hair. The two agents (a) and (b) are different from each other.

Accordingly, a method for dyeing keratinous material, in particular human hair, is disclosed, comprising the following steps:
  application of an agent (a) to the keratinous material, the agent (a) comprising at least one organic silicon compound, and
  Application of an agent (b) to the keratinous material, wherein the agent (b) comprises:
  (b1) at least one color-imparting compound comprising at least one pigment based on a lenticular substrate platelet, and
  (b2) and at least one film-forming polymer, where the two agents (a) and (b) are different from each other.

Agent (a)

Agent (a) is exemplified by its content of at least one organic silicon compound, in particular at least one organic silane. The organic silicon compounds or organic silanes included in agent (a) are reactive compounds.

Composition (a) comprises the organic silicon compound(s), in particular the organic silane(s), in a cosmetic carrier which may be hydrated, low in water or anhydrous. In addition, the cosmetic carrier can be liquid, gel-like, creamy, pasty, powdery or even solid (e.g., in the form of a tablet or a pressed product). Preferably, the cosmetic carrier of the product (a) is an aqueous or aqueous-alcoholic carrier. For hair coloring, such carriers are, for example, creams, emulsions, gels, or also surfactant-containing foaming solutions, such as shampoos, foam aerosols, foam formulations or other preparations suitable for application to the hair.

The cosmetic carrier preferably contains water, which means that the carrier contains at least about 2% by weight of water based on its weight. Preferably, the water content is above about 5 wt. %, further preferably above about 10 wt. %, still further preferably above about 15 wt. %. The cosmetic carrier can also be aqueous alcoholic. Aqueous/alcoholic solutions in the context of the present disclosure are aqueous solutions containing about 2 to about 70% by weight of a C1-C4 alcohol, more particularly ethanol or isopropanol. The agents may additionally contain other organic solvents, such as methoxybutanol, benzyl alcohol, ethyl diglycol or 1,2-propylene glycol. Preferred are all water-soluble organic solvents.

The term "coloring agent" is used in the context of the present disclosure to refer to a coloring of keratinous material, in particular human hair, brought about using pigments and/or direct dyes. During this coloring process, the coloring compounds are deposited in a particularly homogeneous and smooth film on the surface of the keratinous material or diffuse into the keratinous fiber. The film is formed in situ by oligomerization or polymerization of the organic silicon compound(s), and by the interaction of organic silicon compound with the colorant compounds.

Organic Silicon Compounds

As an essential ingredient of the present disclosure, the agent (a) contains at least one organic silicon compound. Preferred organic silicon compounds are selected from silanes having one, two or three silicon atoms.

Organic silicon compounds, alternatively called organosilicon compounds, are compounds which either have a direct silicon-carbon bond (Si—C) or in which the carbon is bonded to the silicon atom via an oxygen, nitrogen, or sulfur atom. The organic silicon compounds of the present disclosure are preferably compounds containing one to three silicon atoms. Organic silicon compounds preferably contain one or two silicon atoms.

The agent (a) particularly preferably contains at least one organic silicon compound selected from silanes having one, two or three silicon atoms.

According to IUPAC rules, the term silane stands for a group of chemical compounds based on a silicon skeleton and hydrogen. In organic silanes, the hydrogen atoms are completely or partially replaced by organic groups such as (substituted) alkyl groups and/or alkoxy groups. In organic silanes, some of the hydrogen atoms may also be replaced by hydroxy groups.

In a particularly preferred embodiment, the method is exemplified by the application of an agent (a) to the keratinous material, wherein the agent (a) comprises at least one organic silicon compound selected from silanes having one, two or three silicon atoms.

The agent (a) particularly preferably comprises at least one organic silicon compound selected from silanes having one, two or three silicon atoms, the organic silicon compound further comprising one or more basic chemical functions and one or more hydroxyl groups or hydrolysable groups per molecule.

In a very particularly preferred embodiment, the method is exemplified by the application of an agent (a) to the keratinous material, said agent (a) comprising at least one organic silicon compound selected from silanes having one, two or three silicon atoms, said organic silicon compound further comprising one or more basic chemical functions and one or more hydroxyl groups or hydrolysable groups per molecule.

This basic group can be, for example, an amino group, an alkylamino group or a dialkylamino group, which is preferably connected to a silicon atom via a linker. Preferably, the basic group is an amino group, a $C_1$-$C_6$ alkylamino group or a di($C_1$-$C_6$)alkylamino group.

The hydrolysable group(s) is (are) preferably a $C_1$-$C_6$ alkoxy group, especially an ethoxy group or a methoxy group. It is preferred when the hydrolysable group is directly bonded to the silicon atom. For example, if the hydrolysable group is an ethoxy group, the organic silicon compound preferably comprises a structural unit R'R"R'"Si—O—$CH_2$—$CH_3$. The radicals R', R" and R'" represent the three remaining free valences of the silicon atom.

A very particularly preferred method is exemplified in that the agent (a) contains at least one organic silicon compound selected from silanes having one, two or three silicon atoms, the organic silicon compound preferably comprising one or more basic chemical functions and one or more hydroxyl groups or hydrolysable groups per molecule.

Particularly good results were obtained when the agent (a) contains at least one organic silicon compound of formula (I) and/or (II).

In another very particularly preferred embodiment, a method is exemplified in that an agent (a) is applied to the keratinous material or human hair, wherein the agent (a) comprises at least one organic silicon compound (a) of formula (I) and/or (II), $$R_1R_2N\text{-}L\text{-}Si(OR_3)_a(R_4)_b \qquad (I),$$

where
$R_1$, $R_2$ independently represent a hydrogen atom or a $C_1$-$C_6$ alkyl group,
L is a linear or branched divalent $C_1$-$C_{20}$ alkylene group,
$R_3$ is a hydrogen atom or a $C_1$-$C_6$ alkyl group,
$R_4$ represents a $C_1$-$C_6$ alkyl group
a, stands for an integer from 1 to 3, and
b stands for the integer 3-a, $$(R_5O)_c(R_6)_dSi\text{-}(A)_e\text{-}[NR_7\text{-}(A')]_f\text{-}[O\text{-}(A'')]_g\text{-}[NR_8\text{-}(A''')]_h\text{-}Si(R_{6'})_{d'}(OR_{5'})_{e'} \qquad (II),$$

where
R5, R5', R5" independently represent a hydrogen atom or a $C_1$-$C_6$ alkyl group,
R6, R6' and R6" independently represent a $C_1$-$C_6$ alkyl group,
A, A', A", independently of one another represent a linear or branched divalent $C_1$-$C_2$ alkylene group
$R_7$ and $R_8$ independently represent a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group or a group of formula (III)

$$(A'''')\text{-}Si(R_{6''})_{d''}(OR_{5''})_{c''} \qquad (III),$$

c, stands for an integer from 1 to 3,
d stands for the integer 3-c,
c' stands for an integer from 1 to 3,
d' stands for the integer 3-c',
c" stands for an integer from 1 to 3,
d" stands for the integer 3-c",
e stands for 0 or 1,
f stands for 0 or 1,
g stands for 0 or 1,
h stands for 0 or 1,
provided that at least one of e, f, g, and h is different from 0.

The substituents $R_1$, $R_2$, $R_3$, $R_4$, $R_5$, $R_{5'}$, $R_{5''}$, $R_6$, $R_{6'}$, $R_{6''}$, $R_7$, $R_8$, L, A, A', A", A''' and A'''' in the compounds of formula (I) and (II) are explained below as examples: Examples of a $C_1$-$C_6$ alkyl group are the groups methyl, ethyl, propyl, isopropyl, n-butyl, s-butyl, and t-butyl, n-pentyl and n-hexyl. Propyl, ethyl, and methyl are preferred alkyl radicals. Examples of a $C_2$-$C_6$ alkenyl group are vinyl, allyl, but-2-enyl, but-3-enyl and isobutenyl, preferred $C_2$-$C_6$ alkenyl radicals are vinyl and allyl. Preferred examples of a hydroxy $C_1$-$C_6$ alkyl group are a hydroxymethyl, a 2-hydroxyethyl, a 2-hydroxypropyl, a 3-hydroxypropyl, a 4-hydroxybutyl group, a 5-hydroxypentyl and a 6-hydroxyhexyl group; a 2-hydroxyethyl group is particularly preferred. Examples of an amino $C_1$-$C_6$ alkyl group are the aminomethyl group, the 2-aminoethyl group, the 3-aminopropyl group. The 2-aminoethyl group is particularly preferred. Examples of a linear divalent $C_1$-$C_{20}$ alkylene group include the methylene group (—$CH_2$), the ethylene group (—$CH_2$—$CH_2$—), the propylene group (—$CH_2$—$CH_2$—$CH_2$—) and the butylene group (—$CH_2$—$CH_2$—$CH_2$—$CH_2$—). The propylene group (—$CH_2$—$CH_2$—$CH_2$—) is particularly preferred. From a chain length of 3 C atoms, divalent alkylene groups can also be branched. Examples of branched divalent $C_3$-$C_{20}$ alkylene groups are (—$CH_2$—CH($CH_3$)—) and (—$CH_2$—CH($CH_3$)—$CH_2$—).

In the organic silicon compounds of the formula (I)

$$R_1R_2N\text{-}L\text{-}Si(OR_3)_a(R_4)_b \qquad (I),$$

the radicals $R_1$ and $R_2$ independently of one another represent a hydrogen atom or a $C_1$-$C_6$ alkyl group. Very preferably, $R_1$ and $R_2$ both represent a hydrogen atom.

In the middle part of the organic silicon compound is the structural unit or the linker -L- which stands for a linear or branched, divalent $C_1$-$C_{20}$ alkylene group.

Preferably -L- stands for a linear, divalent $C_1$-$C_{20}$ alkylene group. Further preferably -L- stands for a linear divalent $C_1$-$C_6$ alkylene group. Particularly preferred -L- stands for a methylene group ($CH_2$—), an ethylene group (—$CH_2$—$CH_2$—), propylene group (—$CH_2$—$CH_2$—$CH_2$—) or butylene (—$CH_2$—$CH_2$—$CH_2$—$CH_2$—). L stands for a propylene group (—$CH_2$—$CH_2$—$CH_2$—)

The organic silicon compounds of formula (I)

$$R_1R_2N\text{-}L\text{-}Si(OR_3)_a(R_4)_b \qquad (I),$$

each carries the silicon-containing group —$Si(OR_3)_a(R_4)_b$ on one end.

In the terminal structural unit —$Si(OR_3)_a(R_4)_b$, $R_3$ is hydrogen or $C_1$-$C_6$ alkyl group, and $R_4$ is $C_1$-$C_6$ alkyl group. Particularly preferred, $R_3$ and $R_4$ independently of each other represent a methyl group or an ethyl group.

Here a stands for an integer from 1 to 3, and b stands for the integer 3-a. If a stands for the number 3, then b is equal to 0. If a stands for the number 2, then b is equal to 1. If a stands for the number 1, then b is equal to 2.

Dyeing's with the best wash fastnesses could be obtained if the agent (a) contains at least one organic silicon compound of formula (I) in which the radicals $R_3$, $R_4$ independently of one another represent a methyl group or an ethyl group.

Furthermore, dyeing's with the best wash fastnesses could be obtained if the agent (a) contains at least one organic silicon compound of the formula (I) in which the radical a represents the number 3. In this case the residue b stands for the number 0.

In another preferred embodiment, the method is exemplified in that the agent (a) comprises at least one organic silicon compound of formula (I),
where
$R_3$, $R_4$ independently of one another represent a methyl group or an ethyl group and
a stands for the number 3 and
b stands for the number 0.

In another preferred embodiment, the method is exemplified in that the agent (a) comprises at least one organic silicon compound of formula (I), $$R_1R_2N\text{-}L\text{-}Si(OR_3)_a(R_4)_b \qquad (I),$$

where
$R_1$, $R_2$ both represent a hydrogen atom, and
L represents a linear, divalent $C_1$-$C_6$-alkylene group, preferably a propylene group (—$CH_2$—$CH_2$—$CH_2$—) or an ethylene group (—$CH_2$—$CH_2$—), $R_3$ represents a hydrogen atom, an ethyl group, or a methyl group, $R_4$ represents a methyl group or an ethyl group, a stands for the number 3 and b stands for the number 0.

When b is 0, the radical $R_4$ does not occur in the compounds of formula (I). Accordingly, in a further preferred embodiment, the method is exemplified in that the agent (a) comprises at least one organic silicon compound of formula (I),

where $R_1$, $R_2$ both represent a hydrogen atom, and

L represents a linear, divalent $C_1$-$C_6$-alkylene group, preferably a propylene group (—$CH_2$—$CH_2$—$CH_2$—) or an ethylene group (—$CH_2$—$CH_2$—), $R_3$ represents a hydrogen atom, an ethyl group, or a methyl group, a stands for the number 3 and b stands for the number 0.

Organic silicon compounds of the formula (I) which are particularly suitable for solving the problem are

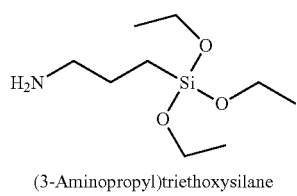

(3-Aminopropyl)triethoxysilane

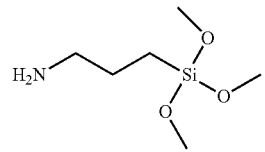

(3-Aminopropyl)trimethoxysilane

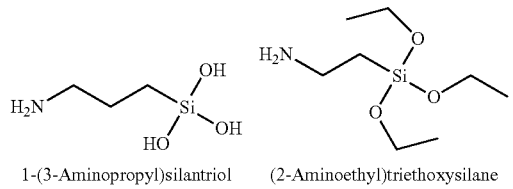

1-(3-Aminopropyl)silantriol     (2-Aminoethyl)triethoxysilane

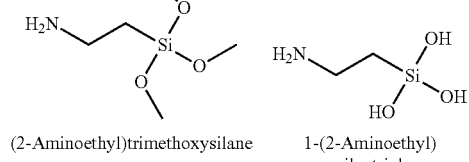

(2-Aminoethyl)trimethoxysilane     1-(2-Aminoethyl) silantriol

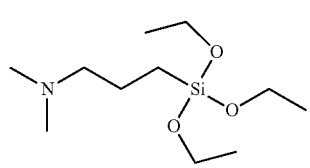

(3-Dimethylaminopropyl) triethoxysilane

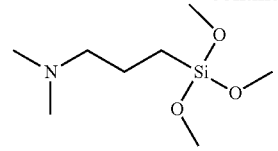

(3-Dimethylaminopropyl) trimethoxysilane silane

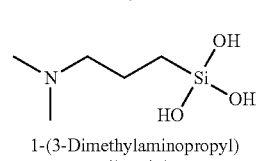 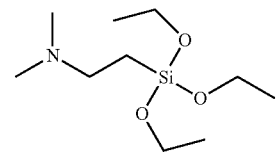

1-(3-Dimethylaminopropyl) silantriol     (2-Dimethylaminoethyl) triethoxysilane

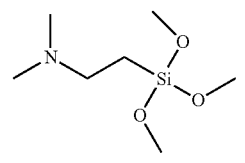 and/or 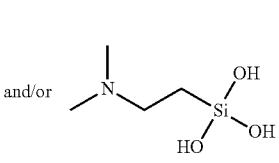

(2-Dimethylaminoethyl) trimethoxysilane     1-(2-Dimethylaminoethyl) silantriol

In a further preferred embodiment, the method is exemplified in that the agent (a) comprises at least one organic silicon compound of formula (I) selected from the group of
(3-Aminopropyl)triethoxysilane
(3-Aminopropyl)trimethoxysilane
1-(3-Aminopropyl)silantriol
(2-Aminoethyl)triethoxysilane
(2-Aminoethyl)trimethoxysilane
1-(2-Aminoethyl)silantriol
(3-Dimethylaminopropyl)triethoxysilane
(3-Dimethylaminopropyl)trimethoxysilane
1-(3-Dimethylaminopropyl)silantriol
(2-Dimethylaminoethyl)triethoxysilane.
(2-Dimethylaminoethyl)trimethoxysilane,
1-(2-Dimethylaminoethyl)silantriol
and mixtures thereof.

The organic silicon compound of formula (I) is commercially available.

(3-aminopropyl)trimethoxysilane, for example, can be purchased from Sigma-Aldrich®. (3-aminopropyl)triethoxysilane is also commercially available from Sigma-Aldrich®.

In a further embodiment, the agent (a) comprises at least one organic silicon compound of formula (II)

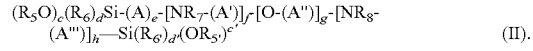

The organosilicon compounds of formula (II) each bear at their two ends the silicon-comprising groupings $(R_5O)_c(R_6)_dSi$— and —$Si(R_{6'})_{d'}(OR_{5'})_{c'}$.

In the central part of the molecule of formula (II) there are the groups -(A)$_e$- and —[NR$_7$-(A')]$_f$- and —[O-(A")]$_g$- and —[NR$_8$-(A''')]$_h$-. Here, each of the radicals e, f, g, and h can independently of one another stand for the number 0 or 1, with the proviso that at least one of the radicals e, f, g, and h is different from 0. In other words, an organic silicon compound of formula (II) contains at least one grouping from the group of -(A)- and —[NR$_7$-(A')]- and —[O-(A")]- and —[NR$_8$-(A''')]-.

In the two terminal structural units $(R_5O)_c(R_6)_dSi$— and —$Si(R_{6'})_{d'}(OR_{5'})_{c'}$, the radicals R5, R5', R5" independently of one another represent a hydrogen atom or a $C_1$-$C_6$ alkyl group. The radicals R6, R6' and R6" independently represent a $C_1$-$C_6$ alkyl group.

Here d stands for an integer from 1 to 3, and d stands for the integer 3-c. If c stands for the number 3, then d is equal to 0. If c stands for the number 2, then d is equal to 1. If c stands for the number 1, then d is equal to 2.

Analogously c' stands for a whole number from 1 to 3, and d' stands for the whole number 3-c'. If c' stands for the number 3, then d' is 0. If c' stands for the number 2, then d' is 1. If c' stands for the number 1, then d' is 2.

Dyeing's with the best wash fastness values could be obtained if the residues c and c' both stand for the number 3. In this case d and d' both stand for the number 0.

In another preferred embodiment, the method is exemplified in that the agent (a) comprises at least one organic silicon compound of formula (II),

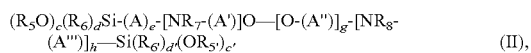

where
R5 and R5' independently represent a methyl group or an ethyl group,
c and c' both stand for the number 3 and
d and d' both stand for the number 0.

If c and c' are both the number 3 and d and d' are both the number 0, the organic silicon compound of the present disclosure corresponds to formula (IIa)

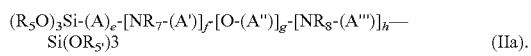

The radicals e, f, g, and h can independently stand for the number 0 or 1, whereby at least one radical from e, f, g, and h is different from zero. The abbreviations e, f, g, and h thus define which of the groupings -(A)$_e$- and —[NR$_7$-(A')]$_f$- and —[O-(A")]$_g$- and —[NR$_8$-(A''')]$_h$- are in the middle part of the organic silicon compound of formula (II).

In this context, the presence of certain groupings has proved to be particularly beneficial in terms of increasing washability. Particularly good results were obtained when at least two of the residues e, f, g, and h stand for the number 1. Especially preferred e and f both stand for the number 1. Furthermore, g and h both stand for the number 0.

If e and f both stand for the number 1 and g and h both stand for the number 0, the organic silicon compounds correspond to formula (IIb)

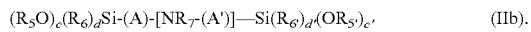

The radicals A, A', A", A''' and A'''' independently represent a linear or branched divalent $C_1$-$C_{20}$ alkylene group. Preferably the radicals A, A', A", A''' and A'''' independently of one another represent a linear, divalent $C_1$-$C_{20}$ alkylene group. Further preferably the radicals A, A', A", A''' and A'''' independently represent a linear divalent $C_1$-$C_6$ alkylene group. In particular, the radicals A, A', A", A''' and A'''' independently of one another represent a methylene group (—CH$_2$—), an ethylene group (—CH$_2$—CH$_2$—), a propylene group (—CH$_2$—CH$_2$—CH$_2$—) or a butylene group (—CH$_2$—CH$_2$—CH$_2$—CH$_2$—). In particular, the radicals A, A', A", A''' and A'''' stand for a propylene group (—CH$_2$—CH$_2$—CH$_2$—).

If the radical f represents the number 1, then the organic silicon compound of formula (II) contains a structural grouping —[NR$_7$-(A')]-.
If the radical h represents the number 1, then the organic silicon compound of formula (II) contains a structural grouping —[NR$_8$-(A''')]-.

Wherein R$_7$ and R$_8$ independently represent a hydrogen atom, a $C_1$-$C_6$ alkyl group, a hydroxy —$C_1$-$C_6$ alkyl group, a $C_2$-$C_6$ alkenyl group, an amino —$C_1$-$C_6$ alkyl group or a group of the formula (III)

Very preferably, R$_7$ and R$_8$ independently represent a hydrogen atom, a methyl group, a 2-hydroxyethyl group, a 2-alkenyl group, a 2-aminoethyl group or a grouping of formula (III).

When the radical f represents the number 1 and the radical h represents the number 0, the organic silicon compound as contemplated herein contains the grouping [NR$_7$-(A')] but not the grouping —[NR$_8$-(A")]. If the radical R$_7$ now stands for a grouping of the formula (III), the agent (a) contains an organic silicon compound with 3 reactive silane groups.

In another preferred embodiment, the method is exemplified in that the agent (a) comprises at least one organic silicon compound of formula (II),

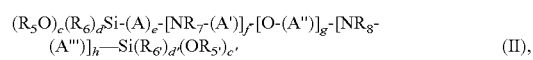

where
e and f both stand for the number 1,
g and h both stand for the number 0,
A and A' independently represent a linear, divalent $C_1$-$C_6$ alkylene group, and
R$_7$ represents a hydrogen atom, a methyl group, a 2-hydroxyethyl group, a 2-alkenyl group, a 2-aminoethyl group or a group of formula (III).

In a further preferred embodiment, the method is exemplified in that the agent (a) comprises at least one organic silicon compound of formula (II), wherein
e and f both stand for the number 1,
g and h both stand for the number 0,
A and A' independently of one another represent a methylene group (—CH$_2$—), an ethylene group (—CH$_2$—CH$_2$—) or a propylene group (—CH$_2$—CH$_2$—CH$_2$—), and
R$_7$ represents a hydrogen atom, a methyl group, a 2-hydroxyethyl group, a 2-alkenyl group, a 2-aminoethyl group or a group of formula (III).

Organic silicon compounds of the formula (II) which are well suited for solving the problem are

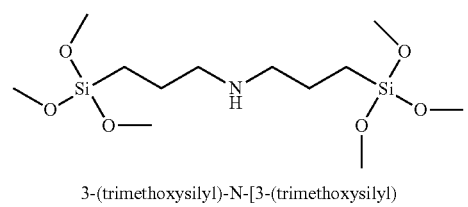

3-(trimethoxysilyl)-N-[3-(trimethoxysilyl)propyl]-1-propanamine

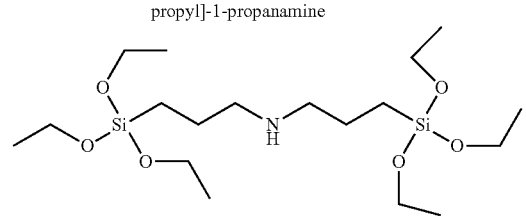

3-(Triethoxysilyl)-N-[3-(triethoxysilyl)propyl]-1-propanamine

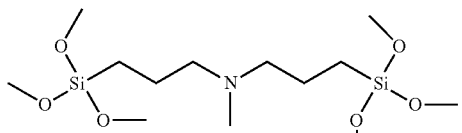

N-methyl-3-(trimethoxysilyl)-N-[3-(trimethoxysilyl)
propyl]-1-propanamine

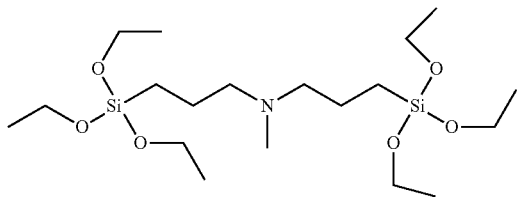

N-Methyl-3-(triethoxysilyl)-N-[3-(triethoxysilyl)
propyl]-1-propanamine

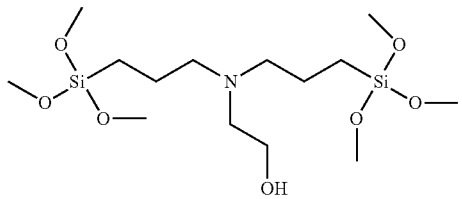

-2-[Bis[3-trimethoxysilyl)propyl]amino]-ethanol

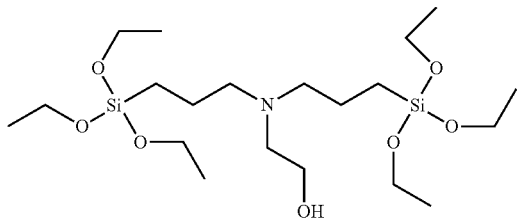

2-[Bis[3-trimethoxysilyl)propyl]amino]-ethanol

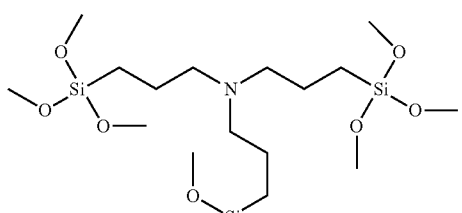

3-(Trimethoxysilyl)-N,N-bis[3-(trimethoxysilyl)
propyl]-1-propanamine

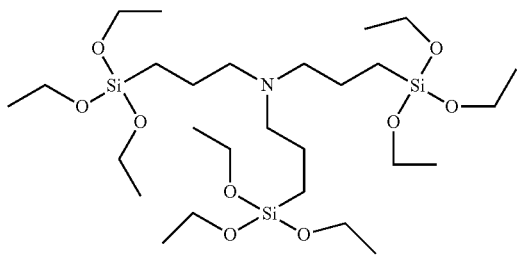

3-(Triethoxysilyl)-N,N-bis[3-(triethoxysilyl)
propyl]-1-propanamine

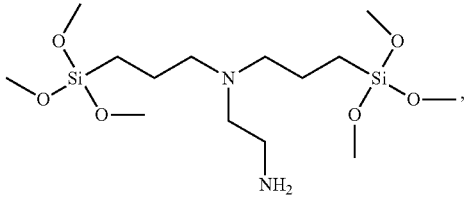

N1,N1-Bis[3-(trimethoxysilyl)propyl]-1,2-ethanediamine

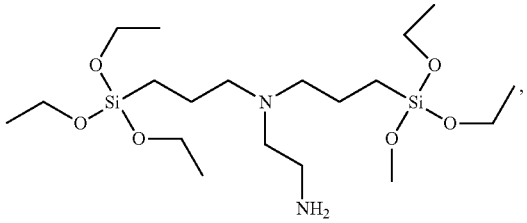

N1,N1-Bis[3-(triethoxysilyl)propyl]-1,2-ethanediamine

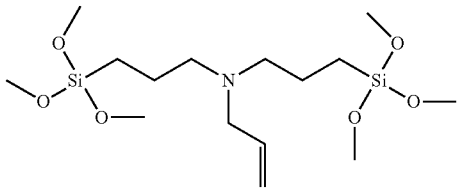

N,N-Bis[3-(trimethoxysilyl)propyl]-2-propen-1-amine

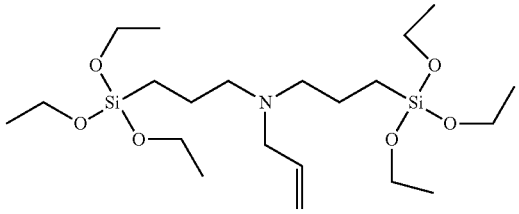

N,N-Bis[3-(triethoxysilyl)propyl]-2-propene-1-amine

The organic silicon compounds of formula (II) are commercially available. Bis(trimethoxysilylpropyl)amines with the CAS number 82985-35-1 can be purchased from Sigma-Aldrich®.

Bis[3-(triethoxysilyl)propyl]amines with the CAS number 13497-18-2 can be purchased from Sigma-Aldrich®, for example.

N-methyl-3-(trimethoxysilyl)-N-[3-(trimethoxysilyl)propyl]-1-propanamine is alternatively referred to as bis(3-trimethoxysilylpropyl)-N-methylamine and can be purchased commercially from Sigma-Aldrich® or Fluorochem.

3-(triethoxysilyl)-N,N-bis[3-(triethoxysilyl)propyl]-1-propanamine with the CAS number 18784-74-2 can be purchased for example from Fluorochem® or Sigma-Aldrich®.

In another preferred embodiment, a method is exemplified in that the agent (a) comprises at least one organic silicon compound of formula (II) selected from the group of:

3-(Trimethoxysilyl)-N-[3-(trimethoxysilyl)propyl]-1-propanamine
3-(Triethoxysilyl)-N-[3-(triethoxysilyl) propyl]-1-propanamine
N-methyl-3-(trimethoxysilyl)-N-[3-(trimethoxysilyl) propyl]-1-propanamine
N-Methyl-3-(triethoxysilyl)-N-[3-(triethoxysilyl) propyl]-1-propanamine
2-[Bis[3-(trimethoxysilyl) propyl]amino]-ethanol
2-[Bis[3-(triethoxysilyl) propyl]amino]ethanol 3-(Trimethoxysilyl)-N,N-bis[3-(trimethoxysilyl) propyl]-1-propanamine
3-(Triethoxysilyl)-N,N-bis[3-(triethoxysilyl) propyl]-1-propanamine
N1,N1-Bis[3-(trimethoxysilyl) propyl]-1,2-ethanediamine,
N1,N1-Bis[3-(triethoxysilyl) propyl]-1,2-ethanediamine,
N,N-Bis[3-(trimethoxysilyl)propyl]-2-propen-1-amine and/or
N,N-Bis[3-(triethoxysilyl)propyl]-2-propen-1-amine.

In further dyeing trials, it has also been found to be particularly advantageous if the agent (a) applied to the keratinous material in the process comprises at least one organic silicon compound of the formula (IV)

  (IV).

The organic silicon compound(s) of formula (IV) may also be referred to as silanes of the alkylalkoxysilane or alkylhydroxysilane type,

  (IV), where
$R_9$ stands for a $C_1$-$C_{18}$ alkyl group,
$R_{10}$ represents a hydrogen atom or a $C_1$-$C_6$ alkyl group,
$R_1$ represents a $C_1$-$C_6$ alkyl group
k is an integer from 1 to 3, and
m stands for the integer 3-k.

In another preferred embodiment, the method is exemplified in that the agent (a) comprises at least one organic silicon compound of formula (IV).

  (IV), where
$R_9$ stands for a $C_1$-$C_{18}$ alkyl group,
$R_{10}$ represents a hydrogen atom or a $C_1$-$C_6$ alkyl group,
$R_1$ represents a $C_1$-$C_6$ alkyl group
k is an integer from 1 to 3, and
m stands for the integer 3-k.

In a further preferred embodiment, the method is exemplified in that the agent (a) comprises, in addition to the organic silicon compound or compounds of formula (I), at least one further organic silicon compound of formula (IV)

  (IV), where
$R_9$ stands for a $C_1$-$C_{18}$ alkyl group,
$R_{10}$ represents a hydrogen atom or a $C_1$-$C_6$ alkyl group,
$R_{11}$ represents a $C_1$-$C_6$ alkyl group
k is an integer from 1 to 3, and
m stands for the integer 3-k.

In a further preferred embodiment, the method is exemplified in that the agent (a) comprises, in addition to the organic silicon compound or compounds of formula (II), at least one further organic silicon compound of formula (IV)

  (IV), where
$R_9$ stands for a $C_1$-$C_{18}$ alkyl group,
$R_{10}$ represents a hydrogen atom or a $C_1$-$C_6$ alkyl group,
$R_1$ represents a $C_1$-$C_6$ alkyl group
k is an integer from 1 to 3, and
m stands for the integer 3-k.

In a further preferred embodiment, the process is exemplified in that the agent (a) contains, in addition to the organic silicon compound or compounds of the formula (I) and/or (II), at least one further organic silicon compound of the formula (IV)

  (IV), where
$R_9$ stands for a $C_1$-$C_{18}$ alkyl group,
$R_{10}$ represents a hydrogen atom or a $C_1$-$C_6$ alkyl group,
$R_{11}$ represents a $C_1$-$C_6$ alkyl group
k is an integer from 1 to 3, and
m stands for the integer 3-k.

In the organic silicon compounds of formula (IV), the radical $R_9$ represents a $C_1$-$C_{18}$ alkyl group. This $C_1$-$C_{18}$ alkyl group is saturated and can be linear or branched. Preferably, $R_9$ represents a linear $C_1$-$C_{18}$ alkyl group. Preferably, $R_9$ represents a methyl group, an ethyl group, an n-propyl group, an n-butyl group, an n-pentyl group, an n-hexyl group, an n-octyl group, an n-dodecyl group or an n-octyldecyl group. Particularly preferably, $R_9$ represents a methyl group, an ethyl group, an n-hexyl group or an n-octyl group.

In the organic silicon compounds of formula (IV), the radical $R_{10}$ represents a hydrogen atom or a $C_1$-$C_6$ alkyl group. Highly preferred $R_{10}$ stands for a methyl group or an ethyl group.

In the organic silicon compounds of form (IV), the radical $R_{11}$ represents a $C_1$-$C_6$ alkyl group. Preferably $R_1$ stands for a methyl group or an ethyl group.

Furthermore, k stands for a whole number from 1 to 3, and m stands for the whole number 3-k. If k stands for the number 3, then m is equal to 0. If k stands for the number 2, then m is equal to 1. If k stands for the number 1, then m is equal to 2.

Dyeing's with the best wash fastnesses were obtained when an agent (a) containing at least one organic silicon compound corresponding to formula (IV): in which the radical k is the number 3, was used in the process. In this case the residue m stands for the number 0.

Organic silicon compounds of the formula (IV) which are particularly suitable for solving the problem as contemplated herein are

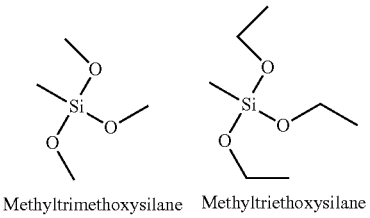

Methyltrimethoxysilane    Methyltriethoxysilane

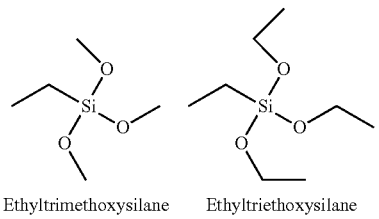

Ethyltrimethoxysilane    Ethyltriethoxysilane

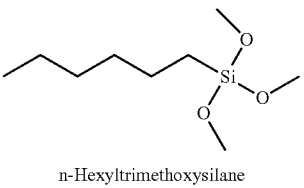

n-Hexyltrimethoxysilane

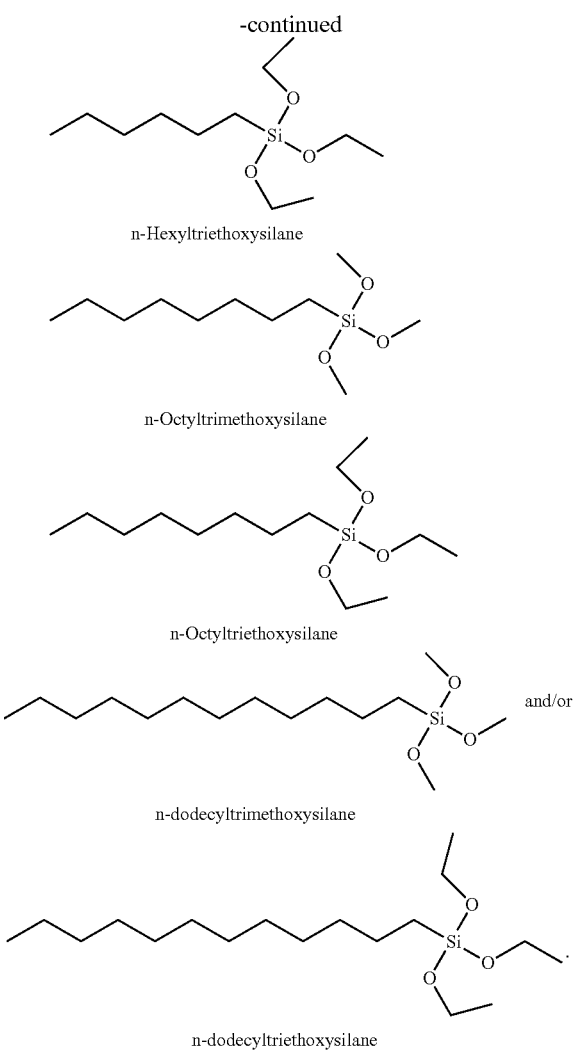

n-octadecyltrimethoxysilane and/or n-octadecyltriethoxysilane.

In a further preferred embodiment, the method is exemplified in that the agent (a) comprises at least one organic silicon compound of formula (IV) selected from the group of:
Methyltrimethoxysilane
Methyltriethoxysilane
Ethyltrimethoxysilane
Ethyltriethoxysilane
Hexyltrimethoxysilane
Hexyltriethoxysilane
Octyltrimethoxysilane
Octyltriethoxysilane
Dodecyltrimethoxysilane
Dodecyltriethoxysilane.
Octadecyltrimethoxysilane and/or
Octadecyltriethoxysilane.

In the course of the work leading to this present disclosure, it was found that particularly stable and uniform films could be obtained on the keratinous material even when the agent (a) contained two organic silicon compounds that were structurally different from each other.

In another preferred embodiment, a method is exemplified in that the agent (a) comprises at least two structurally different organic silicon compounds.

In a preferred embodiment, a process is exemplified in that an agent (a) comprising at least one organic silicone compound of formula (I) and at least one organic silicone compound of formula (IV) is applied to the keratinous material.

In an explicitly quite particularly preferred embodiment, the process is exemplified in that an agent (a) is applied to the keratinous material, which agent contains at least one organic silicon compound of the formula (I) selected from the group of (3-aminopropyl)triethoxysilane and (3-aminopropyl)trimethoxysilane and additionally containing at least one organic silicon compound of formula (IV) selected from the group of methyltrimethoxysilane, methyltriethoxysilane, ethyltrimethoxysilane, ethyltriethoxysilane, hexyltrimethoxysilane and hexyltriethoxysilane.

The organic silicon compounds described above are reactive compounds. In this context, it has been found preferable if the agent (a) contains—based on the total weight of the agent (a)—one or more organic silicon compounds in a total amount of about 0.1 to about 20% by weight, preferably about 0.5 to about 15% by weight and particularly preferably about 5.0 to about 10% by weight.

In this context, it has been found to be particularly preferred if the agent (a) contains—based on the total weight of the agent (a)—one or more organic silicon compounds of the formula (I) and/or (II) in a total amount of about 0.1 to about 20% by weight, preferably about 0.2 to about 15% by weight and particularly preferably about 0.2 to about 3% by weight.

It has further been found to be particularly preferred if the agent (a) comprises -based on the total weight of the agent (a)—one or more organic silicon compounds of the formula (IV) in a total amount of about 0.1 to about 20% by weight, preferably about 0.5 to about 15% by weight and particularly preferably about 2 to about 8% by weight.

Even the addition of small amounts of water leads to hydrolysis in organic silicon compounds with at least one hydrolysable group. The hydrolysis products and/or organic silicon compounds having at least one hydroxy group may react with each other in a condensation reaction. For this reason, both the organosilicon compounds having at least one hydrolysable group and their hydrolysis and/or condensation products may be present in the agent (a). When organosilicon compounds having at least one hydroxyl group are used, both the organic silicon compounds having at least one hydroxyl group and their condensation products may be present in the agent (a).

A condensation product is understood to be a product formed by the reaction of at least two organic silicon compounds each having at least one hydroxyl group or hydrolysable group per molecule with elimination of water and/or with elimination of an alkanol. The condensation products can be, for example, dimers, but also trimers or oligomers, with the condensation products being in equilibrium with the monomers. Depending on the amount of water used or consumed in the hydrolysis, the equilibrium shifts from monomeric organic silicon compounds to condensation product.

Particularly good results were obtained when organic silicon compounds of formula (I) and/or (II) were used in the process. Since, as previously described, hydrolysis/condensation already starts at traces of moisture, the condensation products of the organic silicon compounds (I) and/or (II) are also included in this embodiment.

Particularly resistant strains could be obtained when using an alkaline adjusted agent (a). Preferably, agent (a) comprises water and has a pH of from about 7 to about 11.5, preferably from about 7.5 to about 11, and more preferably from about 8 to about 10.5.

In another very particularly preferred embodiment, the process is exemplified in that the agent (a) has a pH of from about 7 to about 11.5, preferably from about 7.5 to about 11, and particularly preferably from about 8 to about 10.5.

Agent (b)

The agent (b) is exemplified by the presence of at least one color-imparting compound (b1) and at least one film-forming polymer (b2). The color-imparting compound (b1) comprises at least one lenticular substrate platelet-based pigment.

The substrate platelets have an average thickness of at most about 50 nm, preferably less than about 30 nm, particularly preferably at most about 25 nm, for example at most about 20 nm. The average thickness of the substrate platelets is at least about 1 nm, preferably at least about 2.5 nm, particularly preferably at least about 5 nm, for example at least about 10 nm. Preferred ranges for substrate wafer thickness are about 2.5 to about 50 nm, about 5 to about 50 nm, about 10 to about 50 nm; about 2.5 to about 30 nm, about 5 to about 30 nm, about 10 to about 30 nm; about 2.5 to about 25 nm, about 5 to about 25 nm, about 10 to about 25 nm, 2.5 to about 20 nm, about 5 to about 20 nm, and about 10 to about 20 nm. Preferably, each substrate plate has a thickness that is as uniform as possible.

Due to the low thickness of the substrate platelets, the pigment exhibits particularly high hiding power.

The substrate plates have a monolithic structure. Monolithic in this context means a single closed unit without fractures, stratifications, or inclusions, although structural changes may occur within the substrate platelets. The substrate platelets are preferably homogeneously structured, i.e., there is no concentration gradient within the platelets. In particular, the substrate platelets do not have a layered structure and do not have any particles or particles distributed in them.

The size of the substrate platelet can be adjusted to the respective application purpose, especially the desired effect on the keratinic material. Typically, the substrate platelets have an average largest diameter of about 2 to about 200 μm, especially about 5 to about 100 μm.

In a preferred design, the aspect ratio, expressed by the ratio of the average size to the average thickness, is at least about 80, preferably at least about 200, more preferably at least about 500, more preferably more than about 750. The average size of the uncoated substrate platelets is the d50 value of the uncoated substrate platelets. Unless otherwise stated, the d50 value was determined using a Sympatec Helos device with quixel wet dispersion. To prepare the sample, the sample to be analyzed was pre-dispersed in isopropanol for 3 minutes.

The substrate platelets can be composed of any material that can be formed into platelet shape.

They can be of natural origin, but also synthetically produced. Materials from which the substrate platelets can be constructed include metals and metal alloys, metal oxides, preferably aluminum oxide, inorganic compounds, and minerals such as mica and (semi-)precious stones, and plastics. Preferably, the substrate platelets are constructed of metal (alloy).

The metal can be any metal suitable for effect pigments. Such metals include iron and steel, as well as all air and water resistant (semi)metals such as platinum, zinc, chromium, molybdenum and silicon, and their alloys such as aluminum, bronzes and brass. Preferred metals are aluminum, copper, silver, and gold. Preferred substrate platelets include aluminum platelets and brass platelets, with aluminum substrate platelets being particularly preferred.

Lenticular (=lens-shaped) substrate platelets have an essentially regular round edge and are also called "silver-dollars" due to their appearance. Due to their regular structure, the proportion of reflected light predominates in pigments based on lenticular substrate platelets.

The metal or metal alloy substrate plates can be passivated, for example by anodizing (oxide layer) or chromating.

Uncoated lenticular substrate plates, especially those made of metal or metal alloy, reflect incident light to a high degree and produce a light-dark flop but no color impression.

A color impression can be created by optical interference effects, for example. Such pigments can be based on at least single-coated substrate platelets. These show interference effects by superimposing differently refracted and reflected light beams.

Accordingly, preferred pigments are pigments based on a coated lenticular substrate platelet. The substrate wafer preferably has at least one coating B of a highly refractive metal oxide having a coating thickness of at least 50 nm. There is preferably another coating A between the coating B and the surface of the substrate wafer. If necessary, there is a further coating C on the layer B, which is different from the layer B underneath.

Suitable materials for coatings A, B and C are all substances that can be applied to the substrate platelets in a film-like and permanent manner and, in the case of coatings A and B, have the required optical properties. Generally, coating part of the surface of the substrate platelets is sufficient to obtain a pigment with a glossy effect. For example, only the top and/or bottom of the substrate platelets may be coated, with the side surface(s) omitted. Preferably, the entire surface of the optionally passivated substrate platelets, including the side surfaces, is covered by coating B. The substrate platelets are thus completely enveloped by coating B. This improves the optical properties of the pigment and increases its mechanical and chemical resistance. The above also applies to layer A and preferably also to layer C if present.

Although multiple coatings A, B and/or C may be present in each case, the coated substrate wafers preferably have only one coating A, B and, if present, C in each case.

The coating B is composed of at least one highly refractive metal oxide. Highly refractive materials have a refractive index of at least about 1.9, preferably at least about 2.0, and more preferably at least about 2.4. Preferably, the coating B comprises at least about 95 wt. %, more preferably at least about 99 wt. %, in each case based on the total amount of coating, of highly refractive metal oxide(s).

The coating B has a thickness of at least about 50 nm. Preferably, the thickness of coating B is no more than about 400 nm, more preferably no more than about 300 nm.

Highly refractive metal oxides suitable for coating B are preferably selectively light-absorbing (i.e., colored) metal oxides, such as iron(III) oxide (α- and γ-$Fe_2O_3$, red), cobalt (II) oxide (blue), chromium(III) oxide (green), titanium(III) oxide (blue, usually present in admixture with titanium oxynitrides and titanium nitrides) and vanadium(V) oxide (orange), and mixtures thereof. Colorless high-index oxides such as titanium dioxide and/or zirconium oxide are also suitable.

Coating B may contain a selectively absorbing dye, preferably about 0.001 to about 5% by weight, particularly preferably about 0.01 to about 1% by weight, in each case based on the total amount of coating B. Suitable dyes are organic and inorganic dyes which can be stably incorporated into a metal oxide coating.

The coating A preferably has at least one low refractive index metal oxide and/or metal oxide hydrate. Preferably, coating A comprises at least about 95% by weight, more preferably at least about 99% by weight of low-refractive metal oxide (hydrate), in each case based on the total amount of coating A. Low-refractive materials have a refractive index of at most about 1.8, preferably at most about 1.6.

Low refractive index metal oxides suitable for coating A include, for example, silicon (di)oxide, silicon oxide hydrate, aluminum oxide, aluminum oxide hydrate, boron oxide, germanium oxide, manganese oxide, magnesium oxide, and mixtures thereof, with silicon dioxide being preferred. The coating A preferably has a thickness of about 1 to about 100 nm, particularly preferably about 5 to about 50 nm, especially preferably about 5 to about 20 nm.

A particularly preferred pigment based on a lenticular substrate platelet comprises, in addition to a lenticular substrate platelet of aluminum, only a coating A of silica.

Preferably, the distance between the surface of the substrate platelets and the inner surface of coating B is at most about 100 nm, particularly preferably at most about 50 nm, especially preferably at most about 20 nm. By ensuring that the thickness of coating A, and thus the distance between the surface of the substrate platelets and coating B, is within the range specified above, it is possible to ensure that the pigments have a high hiding power.

If the pigment based on a lenticular substrate platelet has only a layer A, it is preferred that the pigment has a lenticular substrate platelet of aluminum and a layer A of silica. If the pigment based on a lenticular substrate platelet has a layer A and a layer B, it is preferred that the pigment has a lenticular substrate platelet of aluminum, a layer A of silica and a layer B of iron oxide.

According to a preferred embodiment, the pigments have a further coating C of a metal oxide (hydrate), which is different from the underlying coating B. Suitable metal oxides include silicon (di)oxide, silicon oxide hydrate, aluminum oxide, aluminum oxide hydrate, zinc oxide, tin oxide, titanium dioxide, zirconium oxide, iron (III) oxide, and chromium (III) oxide. Silicon dioxide is preferred.

The coating C preferably has a thickness of about 10 to about 500 nm, more preferably about 50 to about 300 nm. By providing coating C, for example based on TiO2, better interference can be achieved while maintaining high hiding power.

Layers A and C serve as corrosion protection as well as chemical and physical stabilization. Particularly preferred layers A and C are silica or alumina applied by the sol-gel process. This process comprises dispersing the uncoated lenticular substrate wafer or the lenticular substrate wafer already coated with layer A and/or layer B in a solution of a metal alkoxide such as tetraethyl orthosilicate or aluminum triisopropanolate (usually in a solution of organic solvent or a mixture of organic solvent and water with at least about 50% by weight of organic solvent such as a C1 to C4 alcohol), and adding a weak base or acid to hydrolyze the metal alkoxide, thereby forming a film of the metal oxide on the surface of the (coated) substrate wafer.

Layer B can be produced, for example, by hydrolytic decomposition of one or more organic metal compounds and/or by precipitation of one or more dissolved metal salts, as well as any subsequent post-treatment (for example, transfer of a formed hydroxide-comprising layer to the oxide layers by annealing).

Although each of the coatings A, B and/or C may be composed of a mixture of two or more metal oxide(hydrate)s, each of the coatings is preferably composed of one metal oxide(hydrate).

The pigments based on coated lenticular substrate platelets preferably have a thickness of about 70 to about 500 nm, particularly preferably about 100 to about 400 nm, especially preferably about 150 to about 320 nm, for example about 180 to about 290 nm. Due to the low thickness of the substrate platelets, the pigment exhibits particularly high hiding power. The low thickness of the coated substrate platelets is achieved by keeping the thickness of the uncoated substrate platelets low, but also by adjusting the thicknesses of the coatings A and, if present, C to as small a value as possible. The thickness of coating B determines the color impression of the pigment.

The adhesion and abrasion resistance of pigments based on coated lenticular substrate platelets in keratinic material can be significantly increased by additionally modifying the outermost layer, layer A, B or C depending on the structure, with organic compounds such as silanes, phosphoric acid esters, titanates, borates, or carboxylic acids. In this case, the organic compounds are bonded to the surface of the outermost, preferably metal oxide-comprising, layer A, B, or C. The outermost layer refers to the layer that is spatially farthest from the lenticular substrate platelet. The organic compounds are preferably functional silane compounds that can bind to the metal oxide-comprising layer A, B, or C. These can be either mono- or bifunctional compounds. Examples of bifunctional organic compounds include methacryloxypropenyltrimethoxysilane, 3-methacryloxypropyltrimethoxysilane, 3-acryloxypropyltrimethoxysilane, 2-acryloxyethyltrimethoxysilane, 3-methacryloxypropyltriethoxysilane, 3-acryloxypropyltrimethoxysilane, 2-methacryloxyethyl-triethoxysilane, 2-acryloxyethyltriethoxysilane, 3-methacryloxypropyltris(methox-yethoxy)silane, 3-methacryloxypropyltris(butoxyethoxy)silane, 3-methacryloxy-propyltris(propoxy)silane, 3-methacryloxypropyltris(butoxy)silane, 3-acryloxy-propyltris(methoxyethoxy)silane, 3-acryloxypropyltris(butoxyethoxy)silane, 3-acryl-oxypropyltris(butoxy)silane, vinyltrimethoxysilane, vinyltriethoxysilane, vinylethyl dichlorosilane, vinylmethyldiacetoxysilane, vinylmethyldichlorosilane, vinylmethyldiethoxysilane, vinyltriacetoxysilane, vinyltrichlorosilane, phenylvinyldiethoxysilane, or phenylallyldichlorosilane. Furthermore, a modification with a monofunctional silane, an alkylsilane or arylsilane, can be carried out. This has only one functional group, which can covalently bond to the surface pigment based on coated lenticular substrate platelets (i.e., to the outermost metal oxide-comprising layer) or, if not completely covered, to the metal surface. The hydrocarbon residue of the silane points away from the pigment. Depending on the type and nature of the hydrocarbon residue of the silane, a varying degree of hydrophobicity of the pigment is achieved. Examples of such silanes include hexadecyltrimethoxysilane, propyltrimethoxysilane, etc. Particularly preferred are pigments based on silica-coated aluminum substrate platelets surface-modified with a monofunctional silane. Octyltrimethoxysilane, octyltriethoxysilane, hecadecyltrimethoxysilane and hecadecyltriethoxysilane are particularly preferred. Due to the changed surface properties/hydrophobization, an improvement can be achieved in terms of adhesion, abrasion resistance and alignment in the application.

It has been shown that pigments, based on lenticular substrate platelets, with such a surface modification also exhibit better compatibility with the organosilicon compounds used and/or their condensation or polymerization products.

Particularly good results could be obtained if the agent (b)—based on the total weight of the agent (b)—comprises one or more pigments based on a lenticular substrate platelet in a total amount of about 0.01 to about 10% by weight, preferably about 0.1 to about 8% by weight, more preferably about 0.2 to about 6% by weight and very preferably about 0.5 to about 4.5% by weight.

Pigments based on a lenticular substrate platelet are available, for example, under the name Alegrace® Gorgeous from the company Schlenk® Metallic Pigments GmbH.

Due to their regular structure, dyeing's with pigments based on lenticular substrate platelets exhibit high fastness to rubbing and washing.

In addition to the pigment based on a lenticular substrate platelet, the agent (b) may contain further colorant compounds selected from the group of pigments and/or direct dyes.

Pigments within the meaning of the present disclosure are coloring compounds which have a solubility in water at 25° C. of less than Schlenk 0.5 g/L, preferably less than Schlenk 0.1 g/L, even more preferably less than Schlenk 0.05 g/L. Water solubility can be determined, for example, by the method described below: 0.5 g of the pigment are weighed in a beaker. A stir-fish is added. Then one liter of distilled water is added. This mixture is heated to 25° C. for one hour while stirring on a magnetic stirrer. If undissolved components of the pigment are still visible in the mixture after this period, the solubility of the pigment is below 0.5 g/L. If the pigment-water mixture cannot be assessed visually due to the high intensity of the possibly finely dispersed pigment, the mixture is filtered. If a proportion of undissolved pigments remains on the filter paper, the solubility of the pigment is below 0.5 g/L.

Suitable color pigments can be of inorganic and/or organic origin.

In a preferred embodiment, a process is exemplified in that the agent (b) comprises at least one further colorant compound selected from the group of inorganic and/or organic pigments.

Preferred color pigments are selected from synthetic or natural inorganic pigments. Inorganic color pigments of natural origin can be produced, for example, from chalk, ochre, umber, green earth, burnt Terra di Siena or graphite. Furthermore, black pigments such as iron oxide black, colored pigments such as ultramarine or iron oxide red as well as fluorescent or phosphorescent pigments can be used as inorganic color pigments.

Particularly suitable are colored metal oxides, hydroxides and oxide hydrates, mixed-phase pigments, sulfur-containing silicates, silicates, metal sulfides, complex metal cyanides, metal sulphates, chromates and/or molybdates. Preferred color pigments are black iron oxide (CI 77499), yellow iron oxide (CI 77492), red and brown iron oxide (CI 77491), manganese violet (CI 77742), ultramarine (sodium aluminum sulfo silicates, CI 77007, pigment blue 29), chromium oxide hydrate (CI77289), iron blue (ferric ferrocyanides, CI77510) and/or carmine (cochineal).

Colored pearlescent pigments are also particularly preferred. These are usually mica- and/or mica-based and can be coated with one or more metal oxides. Mica belongs to the layer silicates. The most important representatives of these silicates are muscovite, phlogopite, paragonite, biotite, lepidolite and margarite. To produce the pearlescent pigments in combination with metal oxides, the mica, mainly muscovite or phlogopite, is coated with a metal oxide.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

Also preferred mica-based pigments are synthetically produced mica platelets coated with metal oxide, based on synthetic fluorophlogopite (INCI. Synthetic Fluorphlogopite). The synthetic fluorophlogopite platelets are coated, for example, with tin oxide, iron oxide(s) and/or titanium dioxide. The metal oxide layers may further contain pigments such as ferric hexacyanidoferrate(II/III) or carmine red. Such mica pigments are available, for example, under the name SYNCRYSTAL® from Eckart®.

In a further preferred embodiment, the process is exemplified in that the agent (b) comprises at least one further colorant compound from the group of pigments selected from the group of colored metal oxides, metal hydroxides, metal oxide hydrates, silicates, metal sulfides, complex metal cyanides, metal sulfates, bronze pigments and/or from colored mica- or mica-based pigments coated with at least one metal oxide and/or a metal oxychloride.

In a further preferred embodiment, the process is exemplified in that the agent (b) comprises at least one further colorant compound selected from the group of pigments of mica- or mica-based pigments reacted with one or more metal oxides selected from the group of titanium dioxide (CI 77891), black iron oxide (CI 77499), yellow iron oxide (CI 77492), red and/or brown iron oxide (CI 77491, CI 77499), manganese violet (CI 77742), ultramarines (sodium aluminum sulfosilicates, CI 77007, Pigment Blue 29), chromium oxide hydrate (CI 77289), chromium oxide (CI 77288) and/or iron blue (ferric ferrocyanide, CI 77510).

Other suitable pigments are based on metal oxide-coated platelet-shaped borosilicates. These are coated with tin oxide, iron oxide(s), silicon dioxide and/or titanium dioxide, for example. Such borosilicate-based pigments are available, for example, under the name MIRAGE® from Eckart® or Reflecks® from BASF® SE.

Examples of particularly suitable color pigments are commercially available under the trade names Rona®, Colorona®, Xirona®, Dichrona® and Timiron® from Merck®, Ariabel® and Unipure® from Sensient®, Prestige® from Eckart® Cosmetic Colors, Flamenco®, Cellini®, Cloisonne®, Duocrome®, Gemtone®, Timica®, MultiReflections, Chione from BASF® SE and Sunshine® from Sunstar®.

Particularly preferred color pigments with the trade name Colorona® are, for example:
Colorona® Copper, Merck®, MICA, CI 77491 (IRON OXIDES)
Colorona® Passion Orange, Merck®, Mica, CI 77491 (Iron Oxides), Alumina
Colorona® Patina Silver, Merck®, MICA, CI 77499 (IRON OXIDES), CI 77891 (TITANIUM DIOXIDE)
Colorona® RY, Merck®, CI 77891 (TITANIUM DIOXIDE), MICA, CI 75470 (CARMINE)
Colorona® Oriental Beige, Merck®, MICA, CI 77891 (TITANIUM DIOXIDE), CI 77491 (IRON OXIDES)
Colorona® Dark Blue, Merck®, MICA, TITANIUM DIOXIDE, FERRIC FERROCYANIDE Colorona® Chameleon, Merck®, CI 77491 (IRON OXIDES), MICA
Colorona® Aborigine Amber, Merck®, MICA, CI 77499 (IRON OXIDES), CI 77891 (TITANIUM DIOXIDE)
Colorona® Blackstar Blue, Merck®, CI 77499 (IRON OXIDES), MICA
Colorona® Patagonian Purple, Merck®, MICA, CI 77491 (IRON OXIDES), CI 77891 (TITANIUM DIOXIDE), CI 77510 (FERRIC FERROCYANIDE)
Colorona® Red Brown, Merck®, MICA, CI 77491 (IRON OXIDES), CI 77891 (TITANIUM DIOXIDE)
Colorona® Russet, Merck®, CI 77491 (TITANIUM DIOXIDE), MICA, CI 77891 (IRON OXIDES)
Colorona® Imperial Red, Merck®, MICA, TITANIUM DIOXIDE (CI 77891), D&C RED NO. 30 (CI 73360)
Colorona® Majestic Green, Merck®, CI 77891 (TITANIUM DIOXIDE), MICA, CI 77288 (CHROMIUM OXIDE GREENS)
Colorona® Light Blue, Merck®, MICA, TITANIUM DIOXIDE (CI 77891), FERRIC FERROCYANIDE (CI 77510)
Colorona® Red Gold, Merck®, MICA, CI 77891 (TITANIUM DIOXIDE), CI 77491 (IRON OXIDES)
Colorona® Gold Plus MP 25, Merck®, MICA, TITANIUM DIOXIDE (CI 77891), IRON OXIDES (CI 77491)
Colorona® Carmine Red, Merck®, MICA, TITANIUM DIOXIDE, CARMINE
Colorona® Blackstar Green, Merck®, MICA, CI 77499 (IRON OXIDES)
Colorona® Bordeaux, Merck®, MICA, CI 77491 (IRON OXIDES)
Colorona® Bronze, Merck®, MICA, CI 77491 (IRON OXIDES)
Colorona® Bronze Fine, Merck®, MICA, CI 77491 (IRON OXIDES)
Colorona® Fine Gold MP 20, Merck®, MICA, CI 77891 (TITANIUM DIOXIDE), CI 77491 (IRON OXIDES)
Colorona® Sienna Fine, Merck®, CI 77491 (IRON OXIDES), MICA
Colorona® Sienna, Merck®, MICA, CI 77491 (IRON OXIDES)
Colorona® Precious Gold, Merck®, Mica, CI 77891 (Titanium dioxide), Silica, CI 77491 (Iron oxides), Tin oxide
Colorona® Sun Gold Sparkle MP 29, Merck®, MICA, TITANIUM DIOXIDE, IRON OXIDES, MICA, CI 77891, CI 77491 (EU)
Colorona® Mica Black, Merck®, CI 77499 (Iron oxides), Mica, CI 77891 (Titanium dioxide)
Colorona® Bright Gold, Merck®, Mica, CI 77891 (Titanium dioxide), CI 77491 (Iron oxides)
Colorona® Blackstar Gold, Merck®, MICA, CI 77499 (IRON OXIDES)
Colorona® SynCopper, Merck®, Synthetic Fluorphlogopite (and) Iron Oxides Colorona® SynBronze, Merck®, Synthetic Fluorophlogopite (and) Iron Oxides Other particularly preferred color pigments with the trade name Xirona® are for example:
Xirona® Golden Sky, Merck®, Silica, CI 77891 (Titanium Dioxide), Tin Oxide
Xirona® Caribbean Blue, Merck®, Mica, CI 77891 (Titanium Dioxide), Silica, Tin Oxide
Xirona® Kiwi Rose, Merck®, Silica, CI 77891 (Titanium Dioxide), Tin Oxide
Xirona® Magic Mauve, Merck®, Silica, CI 77891 (Titanium Dioxide), Tin Oxide.
Xirona® Le Rouge, Merck®, Iron Oxides (and) Silica In addition, particularly preferred color pigments with the trade name Unipure® are for example:
Unipure® Red LC 381 EM, Sensient® CI 77491 (Iron Oxides), Silica
Unipure® Black LC 989 EM, Sensient®, CI 77499 (Iron Oxides), Silica
Unipure® Yellow LC 182 EM, Sensient®, CI 77492 (Iron Oxides), Silica Also particularly preferred pigments with the trade name Flamenco® are, for example:
Flamenco® Summit Turquoise T30D, BASF®, Titanium Dioxide (and) Mica
Flamenco® Super Violet 530Z, BASF®, Mica (and) Titanium Dioxide In a further embodiment, the agent (b) may also comprise one or more further colorant compounds selected from the group of organic pigments.

The organic pigments are correspondingly insoluble organic dyes or colorants which may be selected, for example, from the group of nitroso, nitro-azo, xanthene, anthraquinone, isoindolinone, isoindoline, quinacridone, perinone, perylene, diketopyrrolopyorrole, indigo, thioindido, dioxazine and/or triarylmethane compounds.

Examples of particularly suitable organic pigments are carmine, quinacridone, phthalocyanine, sorghum, blue pigments with the Color Index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In another particularly preferred embodiment, the process is exemplified in that the composition (b) comprises at least one further colorant compound from the group of organic pigments selected from the group of carmine, quinacridone, phthalocyanine, sorghum, blue pigments having the Color Index numbers CI 42090, CI 69800, CI 69825, CI 73000, CI 74100, CI 74160, yellow pigments having the Color Index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof.

The organic pigment can also be a color paint. In this disclosure, the term color lacquer means particles comprising a layer of absorbed dyes, the unit of particle and dye being insoluble under the above-mentioned conditions. The particles can, for example, be inorganic substrates, which can be aluminum, silica, calcium borosilate, calcium aluminum borosilicate or even aluminum.

For example, alizarin color varnish can be used.

Due to their excellent light and temperature resistance, the use of the above pigments in the agent (b) of the process is particularly preferred. It is also preferred if the pigments used have a certain particle size. As contemplated herein, it is advantageous if the at least one pigment has a mean particle size $D_{50}$ of from about 1 to about 50 µm, preferably from about 5 to about 45 µm, preferably from about 10 to about 40 µm, from about 14 to about 30 µm. The mean particle size $D_{50}$, for example, can be determined using dynamic light scattering (DLS).

In addition to the pigment based on a lenticular substrate platelet, the agent (b) may contain as further colorant compound(s) (b1) other effect pigments such as pigments based on lamellar substrate platelets or pigments based on VMP substrate platelets. VMP refers to vacuum metallized pigments.

The further pigment or pigments may be used in an amount of from about 0.001 to about 20% by weight, from about 0.05 to about 5% by weight, in each case based on the total weight of the agent (b).

As further coloring compounds, the agents (b) used in the process may also contain one or more direct dyes. Direct-acting dyes are dyes that draw directly onto the hair and do not require an oxidative process to form the color. Direct dyes are usually nitrophenylene diamines, nitroaminophenols, azo dyes, anthraquinones, triarylmethane dyes or indophenols.

The direct dyes within the meaning of the present disclosure have a solubility in water (760 mmHg) at 25° C. of more than about 0.5 g/L and are therefore not to be regarded as pigments. Preferably, the direct dyes within the meaning of the present disclosure have a solubility in water (760 mmHg) at 25° C. of more than about 1.0 g/L.

Direct dyes can be divided into anionic, cationic, and non-ionic direct dyes.

In a further preferred embodiment, a process is exemplified in that the agent (b) comprises at least one anionic, cationic and/or nonionic direct dye as a further coloring compound.

In another preferred embodiment, a process is exemplified in that the agent (b) comprises at least one anionic, cationic and/or nonionic direct dye.

Suitable cationic direct dyes include Basic Blue 7, Basic Blue 26, Basic Violet 2, and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51, and/or Basic Red 76

As non-ionic direct dyes, non-ionic nitro and quinone dyes and neutral azo dyes can be used. Suitable non-ionic direct dyestuffs are those listed under the international designations or Trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethyl-amino-4-nitrophenol.

In a further preferred embodiment, the process is exemplified in that the agent (b) comprises at least one direct dye selected from the group of anionic, cationic, and nonionic direct dyes.

In the course of the work leading to the present disclosure, it has been found that dyeing's of particularly high color intensity can be produced with agents (b) containing at least one anionic direct dye.

In an explicitly quite particularly preferred embodiment, an agent (b) used in the process is therefore exemplified in that it comprises at least one anionic direct dye.

Anionic direct dyes are also called acid dyes. Acid dyes are direct dyes that have at least one carboxylic acid group (—COOH) and/or one sulphonic acid group (—SO$_3$H). Depending on the pH value, the protonated forms (—COOH, —SO$_3$H) of the carboxylic acid or sulphonic acid groups are in equilibrium with their deprotonated forms (—OO—, —SO$_3$— present). The proportion of protonated forms increases with decreasing pH. If direct dyes are used in the form of their salts, the carboxylic acid groups or sulphonic acid groups are present in deprotonated form and are neutralized with corresponding stoichiometric equivalents of cations to maintain electro neutrality. Acid dyes can also be used in the form of their sodium salts and/or their potassium salts.

The acid dyes within the meaning of the present disclosure have a solubility in water (760 mmHg) at 25° C. of more than about 0.5 g/L and are therefore not to be regarded as pigments. Preferably the acid dyes within the meaning of the present disclosure have a solubility in water (760 mmHg) at 25° C. of more than about 1.0 g/L.

The alkaline earth salts (such as calcium salts and magnesium salts) or aluminum salts of acid dyes often have a lower solubility than the corresponding alkali salts. If the solubility of these salts is below about 0.5 g/L (25° C., 760 mmHg), they do not fall under the definition of a direct dye.

An essential characteristic of acid dyes is their ability to form anionic charges, whereby the carboxylic acid or sulphonic acid groups responsible for this are usually linked to different chromophoric systems. Suitable chromophoric systems can be found, for example, in the structures of nitrophenylenediamines, nitroaminophenols, azo dyes, anthraquinone dyes, triarylmethane dyes, xanthene dyes, rhodamine dyes, oxazine dyes and/or indophenol dyes.

In one embodiment of the process, the use of an agent (b) which is exemplified in that it contains at least one anionic direct dye selected from the group of nitrophenylenediamines, nitroaminophenols, azo dyes, anthraquinone dyes, triarylmethane dyes, xanthene dyes, rhodamine dyes, oxazine dyes and/or indophenol dyes is thus preferred, the rhodamine dyes, the oxazine dyes and/or the indophenol dyes, the dyes from the abovementioned group each having at least one carboxylic acid group (—COOH), a sodium carboxylate group (—COONa), a potassium carboxylate group (—COOK), a sulfonic acid group (—SO$_3$H), a sodium sulfonate group (—SO$_3$Na) and/or a potassium sulfonate group (—SO3K).

For example, one or more compounds from the following group can be selected as particularly well suited acid dyes: Acid Yellow 1 (D&C Yellow 7, Citronin A, Ext. D&C Yellow No. 7, Japan Yellow 403, CI 10316, COLIPA n° B001), Acid Yellow 3 (COLIPA n°: C 54, D&C Yellow N° 10, Quinoline Yellow, E104, Food Yellow 13), Acid Yellow 9 (CI 13015), Acid Yellow 17 (CI 18965), Acid Yellow 23 (COLIPA n° C 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA n° C015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodiumsalt; Brown No. 201; RESORCIN BROWN; ACID ORANGE 24; Japan Brown 201; D & C Brown No. 1), Acid Red 14 (C.I. 14720), Acid Red 18 (E124, Red 18; CI 16255), Acid Red 27 (E 123, CI 16185, C-Rot 46, Real Red D, FD&C Red Nr. 2, Food Red 9, Naphthol red S), Acid Red 33 (Red 33, Fuchsia Red, D&C Red 33, CI 17200), Acid Red 35 (CI C.I.18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red n° 106 Pontacyl Brilliant Pink), Acid Red 73 (CI 27290), Acid Red 87 (Eosin, CI 45380), Acid Red 92 (COLIPA n° C53, CI 45410), Acid Red 95 (CI 45425, Erythtosine,Simacid Erythrosine Y), Acid Red 184 (CI 15685), Acid Red 195, Acid Violet 43 (Jarocol Violet 43, Ext. D&C Violet n° 2, C.I. 60730, COLIPA n° C063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent blue AE, Amido blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreenl), Acid Green 5 (CI 42095), Acid Green 9 (C.I.42100), Acid Green 22 (C.I.42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black n° 401, Naphthalene Black 10B, Amido Black 10B, CI 20 470, COLIPA n° B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

The water solubility of direct dyes can be determined, for example, in the following way. 0.1 g of the direct dye is added to a beaker. A stir-fish is added. Then add 100 ml of water. This mixture is heated to 25° C. on a magnetic stirrer while stirring. It is stirred for 60 minutes. The aqueous mixture is then visually assessed. If there are still undissolved residues, the amount of water is increased—for example in steps of 10 ml. Water is added until the amount of dye used is completely dissolved. If the dye-water mixture cannot be assessed visually due to the high intensity of the dye, the mixture is filtered. If a proportion of undissolved dyes remains on the filter paper, the solubility test is repeated with a higher quantity of water. If 0.1 g of the anionic direct dye dissolves in 100 ml water at 25° C., the solubility of the dye is 1.0 g/L.

Acid Yellow 1 is called 8-hydroxy-5,7-dinitro-2-naphthalenesulfonic acid disodium salt and has a solubility in water of at least 40 g/L (25° C.).

Acid Yellow 3 is a mixture of the sodium salts of mono- and disulfonic acids of 2-(2-quinolyl)-1H-indene-1,3(2H)-dione and has a water solubility of 20 g/L (25° C.).

Acid Yellow 9 is the disodium salt of 8-hydroxy-5,7-dinitro-2-naphthalenesulfonic acid, its water solubility is above 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and is highly soluble in water at 25° C.

Acid Orange 7 is the sodium salt of 4-[(2-hydroxy-1-naphthyl)azo]benzene sulphonate. Its water solubility is more than 7 g/L (25° C.).

Acid Red 18 is the trisodium salt of 7-hydroxy-8-[(E)-(4-sulfonato-1-naphthyl)-diazenyl)]-1,3-naphthalenedisulfonate and has a very high-water solubility of more than 20% by weight.

Acid Red 33 is the disodium salt of 5-amino-4-hydroxy-3-(phenylazo)-naphthalene-2,7-disulphonate, its solubility in water is 2.5 g/L (25° C.).

Acid Red 92 is the disodium salt of 3,4,5,6-tetrachloro-2-(1,4,5,8-tetrabromo-6-hydroxy-3-oxoxanthen-9-yl)benzoic acid, whose solubility in water is indicated as greater than 10 g/L (25° C.).

Acid Blue 9 is the disodium salt of 2-({4-[N-ethyl(3-sulfonatobenzyl]amino]phenyl}{4-[(N-ethyl(3-sulfonatobenzyl)imino]-2,5-cyclohexadien-1-ylidene}methyl)-benzenesulfonate and has a solubility in water of more than 20% by weight (25° C.).

A very particularly preferred process is exemplified in that the agent (b) comprises at least one anionic direct dye selected from the group of Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 8, D&C Green 5, D&C Orange 10, D&C Orange 11, D&C Red 21, D&C Red 27, D&C Red 33, D&C Violet 2, D&C Brown 1 and mixtures it contain.

The direct dye(s), in particular the anionic direct dyes, can be used in different amounts in the agent (b) depending on the desired color intensity. Particularly good results could be obtained if the agent (b)—based on the total weight of the agent (b)—comprises one or more direct dyes in a total amount of about '0.01 to about 10% by weight, preferably about 0.1 to about 8% by weight, more preferably about 0.2 to about 6% by weight and very preferably about 0.5 to about 4.5% by weight.

In a further preferred embodiment, a process is exemplified in that the agent (b) contains—based on the total weight of the agent (b)—one or more direct dyes in a total amount of from about 0.01 to about 10% by weight, preferably from about 0.1 to about 8% by weight, more preferably from about 0.2 to about 6% by weight and most preferably from about 0.5 to about 4.5% by weight.

In a further preferred embodiment, a process is exemplified in that the agent (b) contains—based on the total weight of the agent—one or more anionic direct dyes in a total amount of from about 0.01 to about 10% by weight, preferably from about 0.1 to about 8% by weight, more preferably from about 0.2 to about 6% by weight and most preferably from about 0.5 to about 4.5% by weight.

The agent (b) used in the process is further exemplified in that it comprises at least one film-forming polymer (b2).

Polymers are macromolecules with a molecular weight of at least about 1000 g/mol, preferably of at least about 2500 g/mol, particularly preferably of at least about 5000 g/mol, which include identical, repeating organic units. The polymers of the present disclosure may be synthetically produced polymers which are manufactured by polymerization of one type of monomer or by polymerization of different types of monomers which are structurally different from each other. If the polymer is produced by polymerizing one type of monomer, it is called a homo-polymer. If structurally different monomer types are used in polymerization, the resulting polymer is called a copolymer.

The maximum molecular weight of the polymer depends on the degree of polymerization (number of polymerized monomers) and the batch size and is determined by the polymerization method. In terms of the present disclosure, it is preferred if the maximum molecular weight of the film-forming hydrophobic polymer (b) is not more than about $10^7$ g/mol, preferably not more than about $10^6$ g/mol, and particularly preferably not more than about $10^5$ g/mol.

In the sense of the present disclosure, a film-forming polymer is a polymer which can form a film on a substrate, for example on a keratinic material or a keratinic fiber. The formation of a film can be demonstrated, for example, by viewing the polymer-treated keratinous material under a microscope.

The film-forming polymers (b2) in the agent (b) can be hydrophilic or hydrophobic.

In a first embodiment, it may be preferred to use at least one hydrophobic film-forming polymer in agent (b).

A hydrophobic polymer is a polymer that has a solubility in water at 25° C. (760 mmHg) of less than about 1% by weight.

The water solubility of the film-forming, hydrophobic polymer can be determined in the following way, for example. 1 g of the polymer is placed in a beaker. Make up to 100 g with water. A stir-fish is added, and the mixture is heated to 25° C. on a magnetic stirrer while stirring. It is stirred for 60 minutes. The aqueous mixture is then visually assessed. If the polymer-water mixture cannot be assessed visually due to a high turbidity of the mixture, the mixture is filtered. If a proportion of undissolved polymer remains on the filter paper, the solubility of the polymer is less than 1% by weight.

These include acrylic acid-type polymers, polyurethanes, polyesters, polyamides, polyureas, cellulose polymers, nitrocellulose polymers, silicone polymers, acrylamide-type polymers, and polyisoprenes.

Particularly well suited film-forming, hydrophobic polymers are, for example, polymers from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

In a further preferred embodiment, a process is exemplified in that the agent (b) comprises at least one film-forming, hydrophobic polymer (b2) selected from the group of the copolymers of acrylic acid, the copolymers of methacrylic acid, the homopolymers or copolymers of acrylic acid esters, the homopolymers or copolymers of methacrylic acid esters homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

The film-forming hydrophobic polymers, which are selected from the group of synthetic polymers, polymers obtainable by radical polymerization or natural polymers, have proved to be particularly suitable for solving the problem as contemplated herein.

Other particularly well-suited film-forming hydrophobic polymers can be selected from the homopolymers or copolymers of olefins, such as cycloolefins, butadiene, isoprene or styrene, vinyl ethers, vinyl amides, the esters, or amides of (meth)acrylic acid having at least one $C_1$-$C_{20}$ alkyl group, an aryl group or a $C_2$-$C_{10}$ hydroxyalkyl group.

Other film-forming hydrophobic polymers may be selected from the homo- or copolymers of isooctyl (meth)acrylate, isononyl (meth)acrylate, 2-ethylhexyl (meth)acrylate, lauryl (meth)acrylate), isopentyl (meth)acrylate, n-butyl (meth)acrylate), isobutyl (meth)acrylate, ethyl (meth)acrylate, methyl (meth)acrylate, tert-butyl (meth) acrylate, stearyl (meth)acrylate, hydroxyethyl (meth)acrylate, 2-hydroxypropyl (meth)acrylate, 3-hydroxypropyl (meth)acrylate and/or mixtures thereof.

Further film-forming hydrophobic polymers can be selected from the homo- or copolymers of (meth)acrylamide, N-alkyl(meth)acrylamides, in those with $C_2$-$C_{18}$ alkyl groups, such as N-ethyl acrylamide, N-tert-butylacrylamide, le N-octylacrylamide, N-di($C_1$-$C_4$)alkyl(meth)acrylamide.

Other preferred anionic copolymers are, for example, copolymers of acrylic acid, methacrylic acid or their $C_1$-$C_6$ alkyl esters, as they are marketed under the INCI Declaration Acrylates Copolymers. A suitable commercial product is for example Aculyn® 33 from Rohm & Haas. Copolymers of acrylic acid, methacrylic acid or their $C_1$-$C_6$ alkyl esters and the esters of an ethylenically unsaturated acid and an alkoxylated fatty alcohol are also preferred. Suitable ethylenically unsaturated acids are especially acrylic acid, methacrylic acid and itaconic acid; suitable alkoxylated fatty alcohols are especially steareth-20 or ceteth-20.

Very particularly preferred polymers on the market are, for example, Aculyn® 22 (Acrylates/Steareth-20 Methacrylate Copolymer), Aculyn® 28 (Acrylates/Beheneth-25 Methacrylate Copolymer), Structure 2001® (Acrylates/Steareth-20 Itaconate Copolymer), Structure 3001® (Acrylates/Ceteth-20 Itaconate Copolymer), Structure Plus® (Acrylates/Aminoacrylates C10-30 Alkyl PEG-20 Itaconate Copolymer), Carbopol® 1342, 1382, Ultrez 20, Ultrez 21 (Acrylates/C10-30 Alkyl Acrylate Crosspolymer), Synthalen W 2000® (Acrylates/Palmeth-25 Acrylate Copolymer) or the Rohme und Haas distributed Soltex® OPT (Acrylates/C12-22 Alkyl methacrylate Copolymer).

Suitable polymers based on vinyl monomers may include, for example, the homopolymers and copolymers of N-vinylpyrrolidone, vinylcaprolactam, vinyl-(C1-C6)alkyl-pyrrole, vinyl oxazole, vinyl thiazole, vinyl pyrimidine or vinyl imidazole.

Also particularly suitable are the copolymers octylacrylamide/acrylates/butylaminoethyl methacrylate copolymer, such as those sold commercially by NATIONAL STARCH under the trade names AMPHOMER® or LOVOCRYL® 47, or the copolymers of acrylates/octylacrylamides sold under the trade names DERMACRYL® LT and DERMACRYL® 79 by NATIONAL STARCH.

Suitable olefin-based polymers include homopolymers and copolymers of ethylene, propylene, butene, isoprene and butadiene.

In another embodiment, the film-forming hydrophobic polymers may be the block copolymers comprising at least one block of styrene or the derivatives of styrene. These block copolymers may be copolymers comprising one or more blocks in addition to a styrene block, such as styrene/ethylene, styrene/ethylene/butylene, styrene/butylene, styrene/isoprene, styrene/butadiene. Such polymers are commercially distributed by BASF® under the trade name "Luvitol HSB".

Surprisingly, it was found that particularly intense and washfast colorations could be obtained when agent (b) contained at least one film-forming polymer (b2) selected from the group of acrylic acid homopolymers and copolymers, methacrylic acid homopolymers and copolymers, acrylic acid ester homopolymers and copolymers, methacrylic acid ester homopolymers and copolymers, homopolymers and copolymers of acrylic acid amides, homopolymers and copolymers of methacrylic acid amides, homopolymers and copolymers of vinylpyrrolidone, homopolymers and copolymers of vinyl alcohol, homopolymers and copolymers of vinyl acetate, homopolymers and copolymers of ethylene, homopolymers and copolymers of propylene, homopolymers and copolymers of styrene, polyurethanes, polyesters and polyamides.

In a further preferred embodiment, a process is exemplified in that the agent (b) comprises at least one film-forming polymer (b2) selected from the group of the homopolymers and copolymers of acrylic acid, the homopolymers and copolymers of methacrylic acid, the homopolymers and copolymers of acrylic acid esters, the homopolymers and copolymers of methacrylic acid esters, homopolymers and copolymers of acrylic acid amides, homopolymers and copolymers of methacrylic acid amides, homopolymers and copolymers of vinylpyrrolidone, homopolymers and copolymers of vinyl alcohol, homopolymers and copolymers of vinyl acetate, homopolymers and copolymers of ethylene, homopolymers and copolymers of propylene, homopolymers and copolymers of styrene, polyurethanes, polyesters and polyamides.

In a further embodiment, it may be preferred to use at least one hydrophilic film-forming polymer (b2) in the agent (b).

A hydrophilic polymer is a polymer that has a solubility in water at 25° C. (760 mmHg) of more than Luvitol 1% by weight, preferably more than Luvitol 2% by weight.

The water solubility of the film-forming, hydrophilic polymer can be determined in the following way, for example. 1 g of the polymer is placed in a beaker. Make up to 100 g with water. A stir-fish is added, and the mixture is heated to 25° C. on a magnetic stirrer while stirring. It is stirred for 60 minutes. The aqueous mixture is then visually assessed. A completely dissolved polymer appears macroscopically homogeneous. If the polymer-water mixture cannot be assessed visually due to a high turbidity of the mixture, the mixture is filtered. If no undissolved polymer remains on the filter paper, the solubility of the polymer is more than 1% by weight.

Nonionic, anionic, and cationic polymers can be used as film-forming, hydrophilic polymers.

Suitable film-forming hydrophilic polymers may be selected, for example, from the group of polyvinylpyrrolidone (co)polymers, polyvinyl alcohol (co)polymers, vinyl acetate (co)polymers, the carboxyvinyl (co)polymers, the acrylic acid (co)polymers, the methacrylic acid (co)polymers, the natural gums, the polysaccharides and/or the acrylamide (co)polymers.

Furthermore, it is particularly preferred to use polyvinylpyrrolidone (PVP) and/or a vinylpyrrolidone-containing copolymer as film-forming hydrophilic polymer.

In another very particularly preferred embodiment, a process is exemplified in that the agent (b) comprises at least one film-forming hydrophilic polymer selected from the group of polyvinylpyrrolidone (PVP) and the copolymers of polyvinylpyrrolidone.

It is further preferred if the agent contains polyvinylpyrrolidone (PVP) as the film-forming hydrophilic polymer. Surprisingly, the wash fastness of the dyes obtained with PVP-containing agents (b) was also particularly good.

Particularly well-suited polyvinylpyrrolidones are available, for example, under the name Luviskol® K from BASF® SE, especially Luviskol® K 90 or Luviskol® K 85 from BASF® SE.

The polymer PVP K30, which is marketed by Ashland® (ISP, POI Chemical), can also be used as another explicitly very well suited polyvinylpyrrolidone (PVP). PVP K 30 is a polyvinylpyrrolidone which is highly soluble in cold water and has the CAS number 9003-39-8. The molecular weight of PVP K 30 is about 40000 g/mol.

Other particularly suitable polyvinylpyrrolidones are the substances known under the trade names LUVITEC K 17, LUVITEC K 30, LUVITEC K 60, LUVITEC K 80, LUVITEC K 85, LUVITEC K 90 and LUVITEC K 115 and available from BASF®.

The use of film-forming hydrophilic polymers (b2) from the group of copolymers of polyvinylpyrrolidone has also led to particularly good and washfast color results.

Vinylpyrrolidone-vinyl ester copolymers, such as those marketed under the trademark Luviskol® (BASF®), are particularly suitable film-forming hydrophilic polymers. Luviskol® VA 64 and Luviskol® VA 73, both vinylpyrrolidone/vinyl acetate copolymers, are particularly preferred non-ionic polymers.

Of the vinylpyrrolidone-comprising copolymers, a styrene/VP copolymer and/or a vinylpyrrolidone-vinyl acetate copolymer and/or a VP/DMAPA acrylates copolymer and/or a VP/vinyl caprolactam/DMAPA acrylates copolymer are particularly preferred in cosmetic compositions.

Vinylpyrrolidone-vinyl acetate copolymers are marketed under the name Luviskol® VA by BASF® SE. For example, a VP/Vinyl Caprolactam/DMAPA Acrylates copolymer is sold under the trade name Aquaflex® SF-40 by Ashland® Inc. For example, a VP/DMAPA acrylates copolymer is marketed by Ashland® under the name Styleze® CC-10 and is a highly preferred vinylpyrrolidone-comprising copolymer.

Other suitable copolymers of polyvinylpyrrolidone may also be those obtained by reacting N-vinylpyrrolidone with at least one further monomer from the group of V-vinylformamide, vinyl acetate, ethylene, propylene, acrylamide, vinylcaprolactam, vinylcaprolactone and/or vinyl alcohol.

In another very particularly preferred embodiment, a process is exemplified in that the agent (b) comprises at least one film-forming hydrophilic polymer (b2) selected from the group of polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinylcaprolactam copolymers, vinylpyrrolidone/vinylformamide copolymers and/or vinylpyrrolidone/vinyl alcohol copolymers.

Another suitable copolymer of vinylpyrrolidone is the polymer known under the INCI designation maltodextrin/VP copolymer.

Furthermore, intensively colored keratinous material, especially hair, could be obtained with particularly good wash fastness properties when a nonionic film-forming hydrophilic polymer was used as the film-forming hydrophilic polymer.

In another embodiment, the agent (b) may comprise at least one nonionic film-forming hydrophilic polymer (b2).

According to the present disclosure, a non-ionic polymer is understood to be a polymer which in a protic solvent—such as water—under standard conditions does not carry structural units with permanent cationic or anionic groups, which must be compensated by counterions while maintaining electron neutrality. Cationic groups include quaternized ammonium groups but not protonated amines. Anionic groups include carboxylic and sulphonic acid groups.

Preference is given to products containing, as a non-ionic, film-forming, hydrophilic polymer, at least one polymer selected from the group of
Polyvinylpyrrolidone,
Copolymers of N-vinylpyrrolidone and vinyl esters of carboxylic acids containing 2 to 18 carbon atoms of N-vinylpyrrolidone and vinyl acetate,
Copolymers of N-vinylpyrrolidone and N-vinylimidazole and methacrylamide,
Copolymers of N-vinylpyrrolidone and N-vinylimidazole and acrylamide,
Copolymers of N-vinylpyrrolidone with N,N-di(C1 to C4)alkylamino-(C2 to C4)alkyl acrylamide.

If copolymers of N-vinylpyrrolidone and vinyl acetate are used, it is again preferable if the molar ratio of the structural units contained in the monomer N-vinylpyrrolidone to the structural units of the polymer contained in the monomer vinyl acetate is in the range from 20:80 to 80:20, in particular from 30:70 to 60:40. Suitable copolymers of vinyl pyrrolidone and vinyl acetate are available, for example, under the trademarks Luviskol® VA 37, Luviskol® VA 55, Luviskol® VA 64 and Luviskol® VA 73 from BASF® SE. Another particularly preferred polymer is selected from the INCI designation VP/Methacrylamide/Vinyl Imidazole Copolymer, which is available under the trade name Luviset® Clear from BASF® SE.

Another particularly preferred nonionic, film-forming, hydrophilic polymer is a copolymer of N-vinylpyrrolidone and N,N-dimethylaminiopropylmethacrylamide, which is sold, for example, by ISP under the INCI designation VP/DMAPA Acrylates Copolymer, e.g., under the trade name Styleze® CC 10.

A cationic polymer is the copolymer of N-vinylpyrrolidone, N-vinylcaprolactam, N-(3-dimethylaminopropyl) methacrylamide and 3-(methacryloylamino)propyl-lauryl-dimethylammonium chloride (INCI designation: Polyquaternium-69), which is marketed, for example, under the trade name AquaStyle® 300 (28-32 wt. % active substance in ethanol-water mixture, molecular weight 350000) by ISP.

Other suitable film-forming, hydrophilic polymers include
Vinylpyrrolidone-vinylimidazolium methochloride copolymers, as offered under the designations Luviquat® FC 370, FC 550 and the INCI designation Polyquaternium-16 as well as FC 905 and HM 552,
Vinylpyrrolidone-vinylcaprolactam-acrylate terpolymers, as they are commercially available with acrylic acid esters and acrylic acid amides as a third monomer component, for example under the name Aquaflex® SF 40.

Polyquaternium-11 is the reaction product of diethyl sulphate with a copolymer of vinyl pyrrolidone and dimethylaminoethyl methacrylate. Suitable commercial products are available under the names Dehyquart® CC 11 and Luviquat® PQ 11 PN from BASF® SE or Gafquat® 440, Gafquat® 734, Gafquat® 755 or Gafquat® 755N from Ashland® Inc.

Polyquaternium-46 is the reaction product of vinylcaprolactam and vinylpyrrolidone with methylvinylimidazolium methosulfate and is available for example under the name Luviquat® Hold from BASF® SE. Polyquaternium-46 is preferably used in an amount of 1 to 5% by weight—based on the total weight of the cosmetic composition. It is particularly preferred to use polyquaternium-46 in combination with a cationic guar compound. It is even highly preferred that polyquaternium-46 is used in combination with a cationic guar compound and polyquaternium-11.

Suitable anionic film-forming, hydrophilic polymers can be, for example, acrylic acid polymers, which can be in non-crosslinked or crosslinked form. Such products are sold commercially under the trade names Carbopol® 980, 981, 954, 2984 and 5984 by Lubrizol® or under the names Synthalen® M and Synthalen K by 3V Sigma (The Sun Chemicals, Inter Harz).

Examples of suitable film-forming, hydrophilic polymers from the group of natural gums are xanthan gum, gellan gum, carob gum.

Examples of suitable film-forming hydrophilic polymers from the group of polysaccharides are hydroxyethyl cellulose, hydroxypropyl cellulose, ethyl cellulose and carboxymethyl cellulose.

Suitable film-forming, hydrophilic polymers from the group of acrylamides are, for example, polymers prepared from monomers of (meth)acrylamido-C1-C4-alkyl sulfonic acid or salts thereof. Corresponding polymers may be selected from the polymers of polyacrylamidomethanesulfonic acid, polyacrylamidoethanesulfonic acid, polyacrylamidopropanesulfonic acid, poly2-acrylamido-2-methylpropanesulfonic acid, poly-2-methylacrylamido-2-methylpropanesulfonic acid and/or poly-2-methylacrylamido-n-butanesulfonic acid.

Preferred polymers of poly(meth)arylamido-C1-C4-alkyl-sulfonic acids are crosslinked and at least about 90% neutralized. These polymers can be crosslinked or non-crosslinked.

Cross-linked and fully or partially neutralized polymers of the poly-2-acrylamido-2-methylpropane sulfonic acid type are available under the INCI names "Ammonium Polyacrylamido-2-methyl-propanesulphonates" or "Ammonium Polyacryldimethyltauramides".

Another preferred polymer of this type is the crosslinked poly-2-acrylamido-2methyl-propanesulfonic acid polymer sold by Clariant® under the trade name Hostacerin® AMPS, which is partially neutralized with ammonia.

In another explicitly very particularly preferred embodiment, a process is exemplified in that the agent (b) comprises at least one anionic, film-forming, polymer (b2).

In this context, the best results were obtained when the agent (b) contains at least one film-forming polymer (b2) comprising at least one structural unit of formula (P-I) and at least one structural unit of formula (P-II)

(P-I)

$$*+CH_2-CH_2+_n*, \quad \text{(P-II)}$$

where
M is a hydrogen atom or ammonium (NH$_4$), sodium, potassium, ½ magnesium or ½ calcium.

In a further preferred embodiment, a process as contemplated herein is exemplified in that the agent (b) comprises at least one film-forming polymer (b2) which comprises at least one structural unit of the formula (P-I) and at least one structural unit of the formula (P-II)

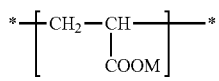

$$*+CH_2-CH_2+_n*, \quad \text{(P-II)}$$

where
M is a hydrogen atom or ammonium (NH$_4$), sodium, potassium, ½ magnesium or ½ calcium.
When M represents a hydrogen atom, the structural unit of the formula (P-I) is based on an acrylic acid unit.
When M stands for an ammonium counterion, the structural unit of the formula (P-I) is based on the ammonium salt of acrylic acid.
When M stands for a sodium counterion, the structural unit of the formula (P-I) is based on the sodium salt of acrylic acid.
When M stands for a potassium counterion, the structural unit of the formula (P-I) is based on the potassium salt of acrylic acid.
If M stands for a half equivalent of a magnesium counterion, the structural unit of the formula (P-I) is based on the magnesium salt of acrylic acid.
If M stands for a half equivalent of a calcium counterion, the structural unit of the formula (P-I) is based on the calcium salt of acrylic acid.

The film-forming polymer or polymers (b2) are preferably used in certain ranges of amounts in the agent (b). In this context, it has proved particularly preferable for solving the problem as contemplated herein if the agent (b) comprises—based on the total weight of the agent (b)—one or more film-forming polymers (b2) in a total amount of from about 0.1 to about 18% by weight, preferably from about 1 to about 16% by weight, more preferably from about 5 to about 14.5% by weight and very particularly preferably from about 8 to about 12% by weight.

In a further preferred embodiment, a process is exemplified in that the agent (b) contains—based on the total weight of the agent (b)—one or more film-forming polymers (b2) in a total amount of from about 0.1 to about 18% by weight, preferably from about 1 to about 16% by weight, more preferably from about 5 to about 14.5% by weight and very particularly preferably from about 8 to about 12% by weight.

Other ingredients in the agents (a) and/or (b)
The agents (a) and (b) described above may also contain one or more optional ingredients.

The agents (a) and/or (b) may additionally contain one or more surfactants. The term surfactants refers to surface-active substances. A distinction is made between anionic surfactants including a hydrophobic residue and a negatively charged hydrophilic head group, amphoteric surfactants, which carry both a negative and a compensating positive charge, cationic surfactants, which in addition to a hydrophobic residue have a positively charged hydrophilic group, and non-ionic surfactants, which have no charges but strong dipole moments and are strongly hydrated in aqueous solution.

Zwitterionic surfactants are those surface-active compounds which carry at least one quaternary ammonium group and at least one —COO$^{(-)}$— or —SO$_3^{(-)}$ group in the molecule. Particularly suitable zwitterionic surfactants are the so-called betaines such as the N-alkyl-N,N-dimethylammonium-glycinate, for example the cocoalkyl-dimethylammoniumglycinate, N-acylaminopropyl-N,N-dimethylammoniumglycinate, for example, cocoacylaminopropyl dimethyl ammonium glycinate, and 2-alkyl-3-carboxymethyl-3-hydroxyethyl imidazolines each having 8 to 18 C atoms in the alkyl or acyl group, and cocoacylaminoethyl hydroxyethyl carboxymethyl glycinate. A preferred zwitterionic surfactant is the fatty acid amide derivative known under the INCI name cocamidopropyl betaine.

Ampholytic surfactants are surface-active compounds which, in addition to a C$_8$-C$_{24}$ alkyl or acyl group in the molecule, contain at least one free amino group and at least one —COOH or —SO$_3$H group and can form internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each with about 8 to 24 C atoms in the alkyl group. Typical examples of amphoteric or zwitterionic surfactants are alkylbetaines, alkylamidobetaines, amino propionates, aminoglycinate, imidazoliniumbetaines and sulfobetaines.

Particularly preferred ampholytic surfactants are N-cocosalkylaminopropionate, cocosacylaminoethylaminopropionate and C$_{12}$-C$_{18}$-acylsarcosine.

The agents (a) and/or (b) may also additionally contain at least one nonionic surfactant. Suitable non-ionic surfactants are alkyl polyglycosides as well as alkylene oxide addition products to fatty alcohols and fatty acids with 2 to 30 mol ethylene oxide per mol fatty alcohol or fatty acid. Preparations with good properties are also obtained if they contain as non-ionic surfactants fatty acid esters of ethoxylated glycerol reacted with at least 2 mol ethylene oxide.

Furthermore, the agents (a) and/or (b) may additionally also contain at least one cationic surfactant. Cationic surfactants are surfactants, i.e., surface-active compounds, each with one or more positive charges. Cationic surfactants contain only positive charges. Usually, these surfactants are composed of a hydrophobic part and a hydrophilic head group, the hydrophobic part usually including a hydrocarbon backbone (e.g., including one or two linear or branched alkyl chains) and the positive charge(s) being in the hydrophilic head group. Examples of cationic surfactants are quaternary ammonium compounds which may carry one or two alkyl chains with a chain length of 8 to 28 carbon atoms as hydrophobic radicals, quaternary phosphonium salts substituted by one or more alkyl chains having a chain length of 8 to 28 carbon atoms or tertiary sulfonium salts.

Furthermore, the cationic charge can also be part of a heterocyclic ring (e.g., an imidazolium ring or a pyridinium ring) in the form of an onium structure. In addition to the functional unit carrying the cationic charge, the cationic surfactant may also contain other uncharged functional groups, as is the case for example with esterquats. The cationic surfactants are used in a total quantity of about 0.1 to about 45 wt. %, preferably about 1 to about 30 wt. % and most preferably about 1 to about 15 wt. %—based on the total weight of the respective agent.

Furthermore, the agents (a) and/or (b) may also contain at least one anionic surfactant. Anionic surfactants are surface-active agents with exclusively anionic charges (neutralized by a corresponding counter cation). Examples of anionic surfactants are fatty acids, alkyl sulphates, alkyl ether sulphates and ether carboxylic acids with 12 to 20 C atoms in the alkyl group and up to 16 glycol ether groups in the molecule.

The anionic surfactants are used in a total quantity of about 0.1 to about 45 wt. %, preferably about 1 to about 30 wt. % and most preferably about 1 to about 15 wt. %—based on the total weight of the respective agent.

To adjust the desired pH value, agents (a) and (b) may also contain at least one alkalizing agent and/or acidifying agent. The pH values for the purposes of the present disclosure are pH values measured at a temperature of 22° C.

As alkalizing agents, agents (a) and/or (b) may contain, for example, ammonia, alkanolamines and/or basic amino acids.

The alkanolamines that can be used in the compositions are preferably selected from primary amines having a $C_2$-$C_6$ alkyl parent carrying at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol.

Particularly preferred alkanolamines are selected from 2-aminoethan-1-ol and/or 2-amino-2-methylpropan-1-ol. A particularly preferred embodiment is therefore exemplified in that an agent (a) and/or (b) contains as alkalizing agent an alkanolamine selected from 2-aminoethan-1-ol and/or 2-amino-2-methylpropan-1-ol.

For the purposes of the present disclosure, an amino acid is an organic compound containing in its structure at least one protonatable amino group and at least one —COOH or one —SO$_3$H group. Preferred amino acids are amino carboxylic acids, especially a-(alpha)-amino carboxylic acids and o-amino carboxylic acids, whereby a-amino carboxylic acids are particularly preferred.

According to the present disclosure, basic amino acids are those amino acids which have an isoelectric point pI of greater than about 7.

Basic a-amino carboxylic acids contain at least one asymmetric carbon atom. In the context of the present disclosure, both possible enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine, and histidine, especially preferably arginine and lysine. In a further particularly preferred embodiment, a process is therefore exemplified in that the alkalizing agent is a basic amino acid selected from the group of arginine, lysine, ornithine and/or histidine.

In addition, agents (a) and/or (b) may contain further alkalizing agents, in particular inorganic alkalizing agents. Applicable inorganic alkalizing agents are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Very particularly preferred alkalizing agents are ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Acidifiers familiar to the skilled person are, for example, organic acids, such as citric acid, acetic acid, maleic acid, lactic acid, malic acid or tartaric acid, and dilute mineral acids, such as hydrochloric acid, sulfuric acid, or phosphoric acid.

The agent (a) and/or agent (b) may further comprise a matting agent. Suitable matting agents include, for example, (modified) starches, waxes, talc and/or (modified) silicas. The amount of matting agent is preferably between about 0.1 and about 10% by weight based on the total amount of agent (a) or agent (b). Preferably, agent (b) comprises a matting agent.

It may be particularly preferred that agent (a) further comprises at least one colorant compound selected from the group of pigments and/or direct dyes.

The colorant compounds from the group of pigments and/or direct dyes which can be used in agent (a) may in principle correspond to the colorant compounds also used in agent (b).

In a more preferred embodiment, the process is exemplified in that the agent (a) comprises at least one colorant compound selected from the group of inorganic and/or organic pigments.

In another particularly preferred embodiment, the process is exemplified in that the composition (a) comprises at least one colorant compound from the group of organic pigments selected from the group of carmine, quinacridone, phthalocyanine, sorghum, blue pigments having the Color Index numbers CI 42090, CI 69800, CI 69825, CI 73000, CI 74100, CI 74160, yellow pigments having the Color Index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof.

The agents (a) and/or (b) may also contain other active ingredients, auxiliaries and additives, such as solvents; fatty ingredients such as $C_5$-$C_{30}$ fatty acid triglycerides, $C_5$-$C_{30}$ fatty acid monoglycerides, $C_5$-$C_{30}$ fatty acid diglycerides and/or hydrocarbons; polymers; structurants such as glucose or sodium chloride, hair conditioning compounds such as phospholipids, for example lecithin and kephalins; perfume oils, dimethyl isosorbide and cyclodextrins; fiber structure-improving active ingredients, in particular mono-, di- and oligosaccharides such as glucose, galactose, fructose, fructose and lactose; dyes for coloring the product; anti-dandruff active ingredients such as piroctone olamine, zinc omadine and climbazole; amino acids and oligopeptides; protein hydrolysates on an animal and/or vegetable basis, as well as in the form of their fatty acid condensation products or optionally anionically or cationically modified derivatives; vegetable oils; light stabilizers and UV blockers; active ingredients such as panthenol, pantothenic acid, pantolactone, allantoin, pyrrolidinonecarboxylic acids and their salts, and bisabolol; Polyphenols, in particular hydroxycinnamic acids, 6,7-dihydroxycoumarins, hydroxybenzoic acids, catechins, tannins, leucoanthocyanidins, anthocyanidins, flavanones, flavones and flavonols; ceramides or pseudoceramides; vitamins, provitamins and vitamin precursors; plant extracts; Fats and waxes such as fatty alcohols, beeswax, montan wax and kerosenes; swelling and penetrating agents such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate as well as PEG-3-distearate; and blowing agents such as propane-butane mixtures, $N_2O$, dimethyl ether, $CO_2$ and air.

The selection of these other substances will be made by the specialist according to the desired properties of the agents. Regarding other optional components and the quantities of these components used, explicit reference is made to the relevant manuals known to the specialist. The additional active ingredients and auxiliaries are preferably used in the agents (a) and/or (b) in amounts of from about 0.0001 to about 25% by weight in each case, from about 0.0005 to about 15% by weight, based on the total weight of the respective agent.

Process for Dyeing Keratinous Materials

In the procedure as contemplated herein, agents (a) and (b) are applied to the keratinous materials, to human hair. Thus, agents (a) and (b) are the ready-to-use agents. The agents (a) and (b) are different.

In principle, agents (a) and (b) can be applied simultaneously or successively, whereby successive application is preferred.

The best results were obtained when agent (a) was applied to the keratinous materials as a pretreatment agent and then agent (b) was applied as a coloring agent.

Therefore, a method for dyeing keratinous material, in particular human hair, comprising the following steps in the order given is particularly preferred:
  in a first step, applying an agent (a) to the keratinous material, the agent (a) comprising at least one organic silicon compound, and
  In a second step, applying an agent (b) to the keratinous material, the agent comprising (b):
(b1) at least one colorant compound comprising at least one lenticular substrate platelet-based pigment, and
(b2) at least one film-forming polymer.

Moreover, to impart a high leaching resistance to the dyed keratinous material over a longer period, agents (a) and (b) are particularly preferably applied within one and the same dyeing process, which means that there is a period of a maximum of several hours between the application of agents (a) and (b).

In a further preferred embodiment, the method is exemplified in that agent (a) is applied first and agent (b) is applied thereafter, the period between the application of agents (a) and (b) being at most about 24 hours, preferably at most about 12 hours and particularly preferably at most about 6 hours.

In the process according to the present disclosure, the keratinous materials, in particular human hair, are first treated with agent (a). Subsequently, the actual colorant (b) -which contains the colorant compounds—is applied to the keratinous materials.

Preferably, agent (a) itself does not contain colorants or coloring compounds. A feature of agent (a) is its content of at least one reactive organic silicon compound. The reactive organic silicon compound(s) (a) functionalize the hair surface as soon as they meet it. In this way a first, still uncolored film is formed. In the second step of the process, a colorant (b) is now applied to the hair. During application of the colorant (b), the colorant compounds interact with the film formed by the organosilicon compounds and are thus bound to the keratinous materials.

In the context of a further form of execution, a procedure comprising the following steps in the order indicated is particularly preferred
(1) Application of the agent (a) on the keratinous material,
(2) Allow the agent (a) to act for a period of about 10 seconds to about 10 minutes, preferably from about 10 seconds to about 5 minutes,
(3) if necessary, rinse the keratinous material with water,
(4) Application of agent (b) on the keratinous material,
(5) Allow the agent (b) to act for a period of about 30 seconds to about 30 minutes, preferably from about 30 seconds to about 10 minutes, and
(6) Rinse the keratinous material with water.

The rinsing of the keratinous material with water in steps (3) and (6) of the process is understood, according to the present disclosure, to mean that only water is used for the rinsing process, without any other agents other than agents (a) and (b).

In step (1), agent (a) is first applied to the keratinous materials, in particular human hair.

After application, the agent (a) is left to act on the keratinous materials. In this context, exposure times of about 10 seconds to about 10 minutes, preferably about 20 seconds to about 5 minutes and most preferably about 30 seconds to about 2 minutes to the keratinous materials, to human hair, have proven to be particularly advantageous.

In a preferred embodiment of the process, the agent (a) can now be rinsed from the keratinic materials before the agent (b) is applied to the hair in the subsequent step.

Dyes with equally good wash fastnesses were obtained when agent (b) was applied to the keratinous materials that were still exposed to agent (a).

In step (4), agent (b) is now applied to the keratinous materials. After application, let the agent (b) act on the hair.

Even with a short contact time of the agent (b), the process allows the production of dyeing's with particularly good intensity and wash fastness. Contact times of about 10 seconds to about 10 minutes, preferably about 20 seconds to about 5 minutes and most preferably about 30 seconds to about 3 minutes on the keratinous materials, on human hair, have proven to be particularly advantageous.

In step (6), the agent (b) (and any agent (a) still present) is now rinsed out of the keratinous material with water.

Multi-Component Packaging Unit (Kit-of-Parts)

In the process as contemplated here, agents (a) and (b) are applied to the keratinous materials, i.e., the two agents (a) and (b) are each the ready-to-use agents.

To increase user comfort, the user is preferably provided with all required resources in the form of a multi-component packaging unit (kit-of-parts).

A second subject of the present disclosure is therefore a multi-component packaging unit (kit-of-parts) for coloring keratinous material, comprehensively packaged separately from one another a first container comprising an agent (a), wherein the agent (a) comprises at least one organic silicon compound, and a second container comprising an agent (b), wherein the agent comprises (b):

(b1) at least one colorant compound comprising at least one lenticular substrate platelet-based pigment, and (b2) at least one film-forming polymer.

The organic silicon compounds included in agent (a) of the kit correspond to the organic silicon compounds that were also used in agent (a) of the method described above.

The colorant compounds from the group of pigments and/or direct dyes included in agent (b) of the kit correspond to the colorant compounds from the group of pigments and/or direct dyes that were also used in agent (b) of the previously described process.

Agent (a) comprises, with the organic silicon compound (s), a class of reactive compounds capable of undergoing hydrolysis and/or oligomerization and/or polymerization in the presence of water as previously described. As a result of their high reactivity, these organic silicon compounds form a film on the keratinous material.

To avoid premature hydrolysis, oligomerization and/or polymerization, it may be preferable to prepare the ready-to-use agent (a) only shortly before use.

In the context of a further embodiment, a multi-component packaging unit (kit-of-parts) for coloring keratinic material is preferably packaged separately from one another a first container comprising an agent (a1), wherein the agent (a1) comprises at least one organic silicon compound, a second container comprising an agent (a2), wherein the agent (a2) comprises water, a third container comprising an agent (b), wherein the agent comprises (b):

(b1) at least one colorant compound comprising at least one lenticular substrate platelet-based pigment, and (b2) at least one film-forming polymer.

To provide a formulation that is as stable as possible during storage, the agent (a1) itself is preferably packaged with low or no water.

In a preferred embodiment, a multicomponent packaging unit (kit-of-parts) is exemplified in that the agent (a1)—based on the total weight of the agent (a1)—has a water content of less than about 10% by weight, preferably of less than about 5% by weight, more preferably of less than about 1% by weight, even more preferably of less than about 0.1% by weight and very particularly preferably of less than about 0.01% by weight.

The agent (a2) contains water. In a preferred embodiment, a multicomponent packaging unit (kit-of-parts) is exemplified in that the agent (a2)—based on the total weight of the agent (a2)—has a water content of from about 15 to 100% by weight, preferably from about 35 to 100% by weight, more preferably from about 55 to 100% by weight, still more preferably from about 65 to 100% by weight and very particularly preferably from about 75 to 100% by weight.

Within this version, the ready-to-use agent (a) is now produced by mixing agents (a1) and (a2).

For example, the user can first mix or shake the agent (a1) comprising the organic silicon compound(s) with the water-containing agent (a2). The user can now apply this mixture of (a1) and (a2)—either directly after its preparation or after a short reaction time of about 10 seconds to about 20 minutes—to the keratinous materials. Afterwards, the user can apply agent (b) as described above.

Regarding the further preferred embodiments of the multicomponent packaging unit, the same applies mutatis mutantis as to the process.

EXAMPLES

1. Formulations

The following formulations have been produced (unless otherwise indicated, all figures are in 0% by weight)

| Pretreatment agent, agent (a) | |
| --- | --- |
| (3-Aminopropyl)triethoxysilane | 2.0 |
| Methyltrimethoxysilane | 7.0 |
| Ammonia/citric acid | ad pH 9.5 |
| Water | ad 100 |

The silanes were mixed with a portion of water, this mixture was left for 30 minutes. Then the pH value was adjusted to the desired value by adding citric acid/ammonia. Water was then added to make up to 100 g.

| Dye, agent (b) | |
| --- | --- |
| Alegrace ® Gorgeous 03-02 (Schlenk Metallic Pigments) | 1 |
| PVP K 30 (Ashland, ISP, Polyvinylpyrrolidone) | 4.5 |
| Dermacryl 79 (Akzo Nobel, Acrylates/Octylacrylamide Copolymer, CAS-Nr. 129702-02-9) | 4.5 |
| Ammonia (25% aqueous solution) | ad pH 10 |
| Water | ad 100 |

2. Application

One strand of hair (Kerling, Euronatural hair white) was dipped into the medium (a) and left in it for 1 minute. Afterwards, excess product (a) was stripped from each strand of hair. Each strand of hair was briefly washed with water. Excess water was scraped off each strand of hair.

Subsequently, the hair strands were each dipped in the agent (b) and left in it for 1 minute. Afterwards, excess agent (b) was stripped from each strand of hair. Each strand of hair was briefly washed with water. Excess water was scraped off each strand of hair.

Subsequently, the strands were visually evaluated. A silver metallic coloring of the hair with high intensity and authenticity was obtained.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for dyeing keratinous material, comprising the following steps:
   applying an agent (a) to the keratinous material, the agent (a) comprising an organic silicon compound, wherein the organic silicon compound comprises a compound of formula (IV);

$$R_9Si(OR_{10})_k(R_{11})m \qquad (IV),$$

wherein
   $R_9$ stands for a $C_1$-$C_{18}$ alkyl group,
   $R_{10}$ represents a hydrogen atom or a $C_1$-$C_6$ alkyl group,
   R11 represents a $C_1$-$C_6$ alkyl group,
   k is an integer from 1 to 3, and
   m stands for the integer 3-k, and
   applying an agent (b) to the keratinous material, wherein the agent (b) comprises:
      (b1) a colorant compound comprising a lenticular substrate platelet-based pigment, and
      (b2) a film-forming polymer.

2. The method according to claim 1, wherein the agent (a) comprises at least one organic silicon compound selected from silanes having one, two or three silicon atoms.

3. The method of claim 1, wherein the lenticular substrate platelet-based pigment comprises a substrate wafer, wherein the substrate wafer comprises a material selected from the group of metals, metal alloys and metal oxides.

4. The method of claim 1, wherein the lenticular substrate platelet-based pigment comprises aluminum.

5. The method according to claim 1, wherein the lenticular substrate platelet-based pigment comprises a coating A of at least one low refractive index metal oxide and/or metal oxide hydrate having a refractive index of at most about 1.8.

6. The method of claim 1, wherein the lenticular substrate platelet-based pigment comprises a coating B of at least one highly refractive metal oxide having a refractive index of at least about 1.9.

7. The method according to 6, wherein the lenticular substrate platelet-based pigment has a further coating C of at least one metal oxide and/or metal oxide hydrate which is different from the underlying coating B.

* * * * *